US006538029B1

(12) United States Patent
Thompson et al.

(10) Patent No.: US 6,538,029 B1
(45) Date of Patent: Mar. 25, 2003

(54) METHODS FOR TREATMENT OF RENAL CELL CARCINOMA

(75) Inventors: W. Joseph Thompson, Doylestown, PA (US); John R. Fetter, North Wales, PA (US); Robert E. Bellet, Elkins Park, PA (US); Han Li, Yardley, PA (US)

(73) Assignee: Cell Pathways, Horsham, PA (US)

( * ) Notice: Subject to any disclaimer, the term of this patent is extended or adjusted under 35 U.S.C. 154(b) by 0 days.

(21) Appl. No.: 10/157,526

(22) Filed: May 29, 2002

(51) Int. Cl.[7] ............................................... A61K 31/19
(52) U.S. Cl. .................... 514/569; 514/231.2; 514/256; 514/277; 514/365; 514/372; 514/381; 514/482; 514/506; 514/520; 514/553; 514/617; 514/618; 514/619; 514/622

(58) Field of Search ................................. 514/617, 618, 514/619, 622, 569, 256, 277, 365, 381, 372, 231.2, 482, 506, 520, 553

(56) References Cited

U.S. PATENT DOCUMENTS 4,994,440 A * 2/1991 Creaven ........................ 514/8
6,087,098 A * 7/2000 McKiernan et al. ........... 435/6

* cited by examiner

*Primary Examiner*—Frederick Krass
(74) *Attorney, Agent, or Firm*—Robert W. Stevenson

(57) ABSTRACT

A method of treating renal cell carcinoma in a mammal with that disease comprising administering to the mammal a physiologically effective amount of an inhibitor of PDE10.

8 Claims, 12 Drawing Sheets

METHODS FOR TREATMENT OF RENAL CELL CARCINOMA

TECHNICAL FIELD

This invention relates to the treatment of renal cell carcinoma.

BACKGROUND OF THE INVENTION

Renal cell carcinoma can progressively develop into widespread metastatic disease. Originating on the surface of the renal cortex, the small, localized primary tumor rarely produces noticeable symptoms during the early stages of disease (e.g., Stages I and II). Early stage renal cell carcinoma is frequently identified incidentally through diagnostic readings performed in the evaluation of an unrelated condition (MRI scans, for example). As the disease progresses, symptoms can present as a classic triad consisting of hematuria, a palpable mass in the flank or abdomen, and pain. In Stages I–III, partial (e.g., Stage I) or total (Stages II and III) surgical removal of the kidney remains the only known effective therapy for localized renal cell carcinoma. Of course, if both kidneys are involved, surgery is usually not an option.

In 30% to 50% of patients, progression to metastatic disease (Stage IV) occurs prior to initial diagnosis. However, traditional therapeutic modalities, including chemotherapy and radiation, are largely ineffective in Stage IV patients. Immunotherapy using interleukin-2 (IL-2) or α-interferon as first-line treatment is a viable option and has been proven to offer an objective response in some patients.

Nonetheless, almost all Stage IV patients are considered incurable. Tumor embolization, external-beam irradiation, and nephrectomy can aid in the palliation of symptoms due to the primary tumor or related ectopic hormone production. There is minimal evidence that nephrectomy induces regression of distant metastases. Thus, nephrectomy, in the hope that it will be followed by spontaneous regression of metastases, is invariably not advised. Spontaneous regressions rarely but occasionally occur. Indeed, a prospective surveillance series of 73 patients with advanced renal cell cancer demonstrated apparent temporary objective regression in 5 (7%) patients without nephrectomy or any therapy. Selected patients with solitary or a limited number of distant metastases can achieve prolonged survival with nephrectomy and surgical resection of the metastases. This has been shown to be the case even for patients with brain metastases. The likelihood of achieving therapeutic benefit with this approach appears enhanced in patients with a long disease-free interval between the initial nephrectomy and the development of metastatic disease.

Responses to cytotoxic chemotherapy generally do not exceed 10% for any regimen that has been studied in adequate numbers of patients. Because of early reports of success, progestational agents have been administered to patients with metastatic renal cell cancer, but the frequency of response is disappointingly low, and there is reportedly no rationale for their use as anticancer therapy. They may offer subjective palliation, however.

Various biologic therapies also have been evaluated. Interferon alfas have approximately a 15% objective response rate in appropriately selected individuals. In general, these patients have non-bulky pulmonary and/or soft tissue metastases with excellent performance status (ECOG 0,1) and no weight loss. The interferon-α doses used in studies reporting good response rates have been in an intermediate range, 6–20 MU-TIW. These responses are rarely complete or durable.

Somewhat more promising are interleukin-2 ("IL-2") treatments. Administration of IL-2 appears to have a similar overall response rate to interferon-α, but with approximately 5% of the appropriately selected patients having durable complete remissions. Combinations of IL-2 and interferon have been studied but reportedly have not been shown to be better than high-dose IL-2 alone. The optimum dose of IL-2 is not completely established. High-dose therapy appears to be associated with higher response rates but with more toxic effects. Low-dose inpatient regimens can reportedly retain efficacy with fewer toxic effects, especially hypotension. Outpatient, subcutaneous administration has also demonstrated responses with acceptable toxic effects. Because of the overall poor results with drug treatment, patients with metastatic renal cell cancer are recommended to be considered for clinical trials, especially phase I and II trials evaluating newer chemotherapeutic agents and biologics such as interferons or IL-2 and strategies to modulate multidrug-resistant phenotype, which is highly expressed in renal cell cancers.

Thus, there is a great need for new, effective therapies for the treatment of renal cell carcinoma.

SUMMARY OF THE INVENTION

This invention represents a novel therapy for treating renal cell carcinoma patients without the substantial side effects of prior pharmaceutical approaches. Specifically, this invention involves the administration of an inhibitor of phosphodiesterase 10 ("PDE10"). Such an inhibitor also advantageously inhibits PDE2 and PDE5.

We surprisingly found that PDE10 is present in renal cell carcinoma, and that its inhibition leads to death of such cells. We are unaware of any reports from prior investigators who claim to have located expressed PDE10 protein in human tissue. To date, investigators have typically located PDE10 message in selected human tissue with little, if any, protein.

DETAILED DESCRIPTION OF THE INVENTION

A. PDE10 Expression in Renal Cell Carcinoma

Renal Cell Carcinoma PDE Isozyme Fractionation and Assay. 786-O cells (a renal cell carcinoma cell line from ATCC) were grown in RPMI 1640, 1 mM pyruvate, 4.5 g/L glucose, 25 mM Hepes, 10% FCS to confluence in 20 150-cm² flasks. Approximately 50 million cells were manually homogenized in a cell breaking buffer containing 20 mM Tris acetate, 5 mM magnesium acetate, 0.1 mM EDTA, 0.5 mM EGTA, 5 mM β-ME, 1.0% Triton X-100, and protease inhibitors (10 mM benzamidine, 10 μM TLCK, 20 nM aprotinin, 2 μM leupeptin, and 2 μM pepstatin A) at pH 7.5 using a glass tissue grinder with a Teflon pestle. After ultracentrifugation at 100,000×g at 4° C. for 1 hour, the supernatant was diluted 5-fold with modified cell breaking buffer without Triton X-100 with containing 5 mM Tris acetate. This sample was loaded at 1 ml/min onto an 18-ml DEAE-Trisacryl M column (BioSepra) using a Pharmacia AKTA/fast protein liquid chromatography system. The column was washed with 8 mM Tris acetate, 5 mM magnesium acetate, and 0.1 mM EDTA, 10% ethylene glycol (pH 7.5), and PDEs eluted with a gradient of 0–1 M sodium acetate in Tris acetate buffer at a flow rate of 1 ml/min into 1.5-ml fractions. [³H]cGMP substrate or [³H]cAMP substrate (0.25 μM; 300,000 dpm) was used to differentiate isozymes, as described previously(Thompson, W. J. et al. *Adv. Cyclic Nucleotide Res* 10, 69–92, 1979.). Reagents were from Sigma except calmodulin (bovine brain) that was from Biomol.

Figure 1:
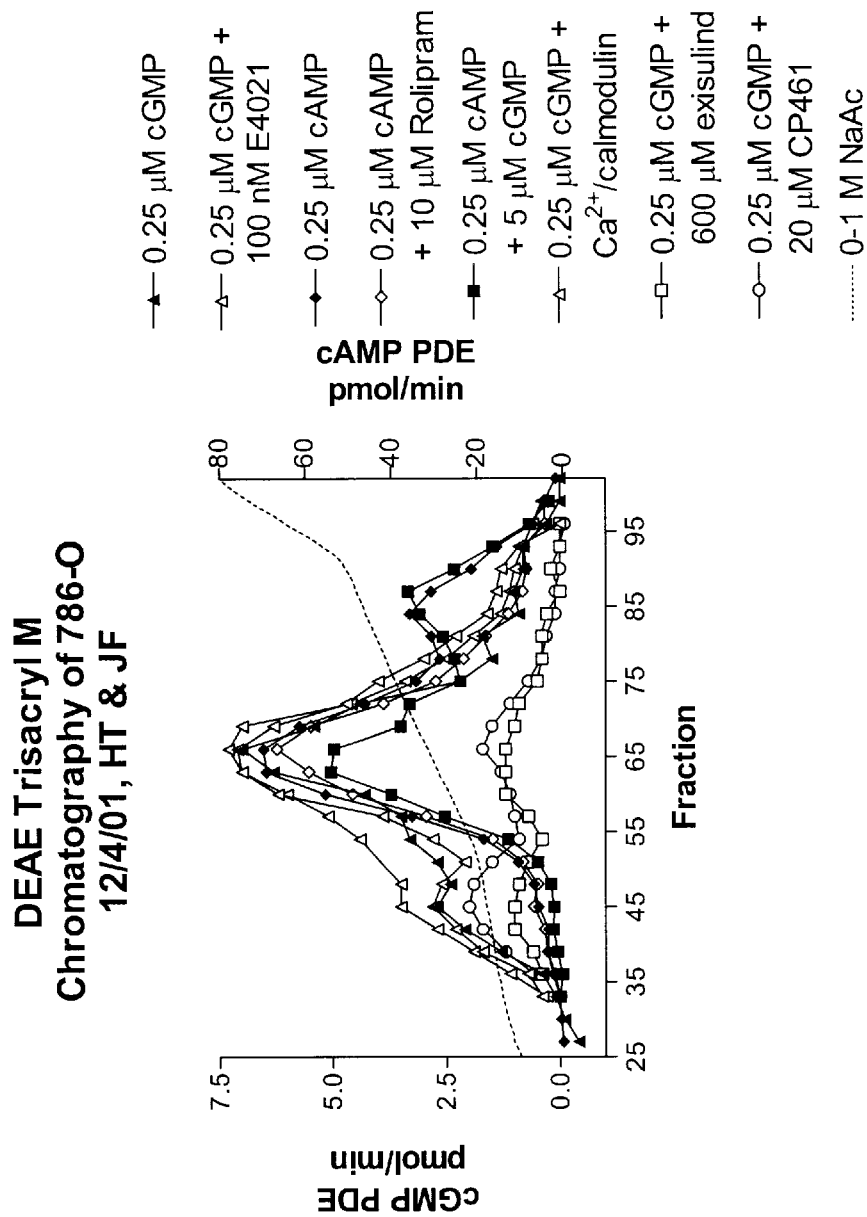
FIG. 1 is a PDE isozyme fractionation and assay. 786-O renal cell carcinoma cells were homogenized and centrifuged at 100,000×g at 4° C. for 1 h. PDE's were fractionated using a DEAE-Trisacryl M column (BioSepra). Assay analysis showed the presence of a PDE with dual substrate affinity for cAMP and cGMP.

As shown in FIG. 1, the assays with cGMP substrate showed a major peak at fraction 65 from the 786-O cells, with a smaller leading peak at fraction 45. This cGMP PDE activity was not inhibited by 100 nM E4021 (a PDE5 inhibitor), indicating the lack of PDE5 in this cell line. Ca2+/calmodulin did not show significant activation, thus indicating a lack of PDE1 activity in these cells. cAMP PDE activity gave overlapping peaks with the cGMP activity, suggesting that both activities could be from a single PDE isoform (e.g., PDE10). A third peak at fraction 85 was inhibited by rolipram, indicating the presence of PDE4 activity in that peak. cAMP activity was partially inhibited by 5 μM cGMP, further supporting that a dual substrate PDE—consistent with PDE10—was present.

Determination of the $IC_{50}$ of cAMP on cGMP PDE Activity of Pooled Fractions from the Center Peak of a 786-O Profile. Fractions were pooled from a 786-O profile from the center peak. Assays were run with cGMP at 5.5 μM substrate. cAMP concentrations were varied to test for inhibition of cGMP PDE activity.

Figure 2:
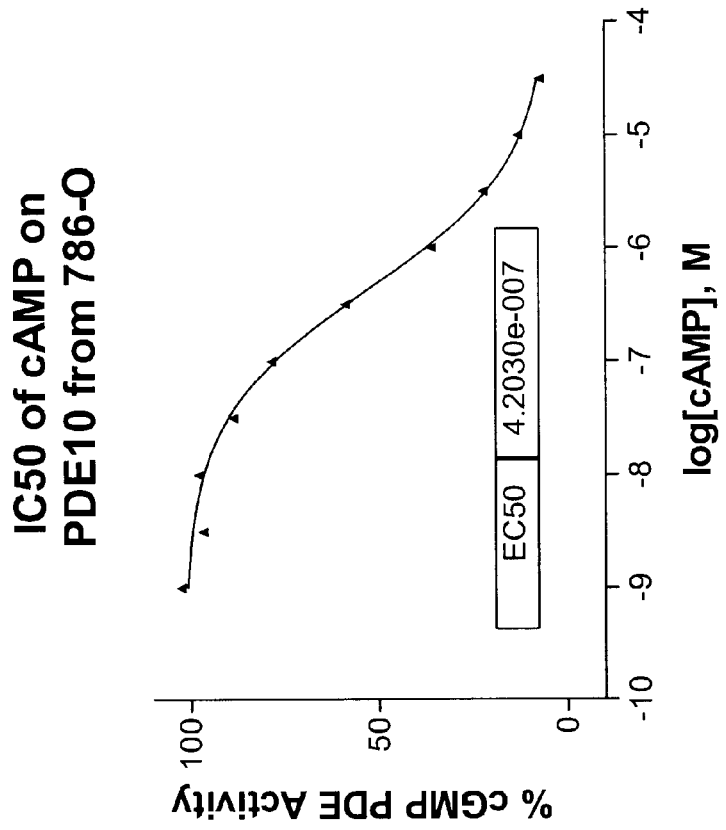
FIG. 2 is a determination of the $IC_{50}$ of cAMP on cGMP PDE activity of pooled fractions from the center peak of a 786-O profile. cAMP inhibited cGMP PDE activity with an $IC_{50}$ of 0.4 μM.

As shown in FIG. 2, cAMP inhibited cGNP PDE activity with an $IC_{50}$ of 0.4 μM. This shows that the PDE in 786-O has dual substrate specificity for cAMP and cGMP, which is consistent with PDE10 activity. This cAMP $IC_{50}$ is comparable to previous $IC_{50}$'s of cloned and expressed human PDE10 enzymes of 0.18 μM, and 0.39 μM (Loughney, K. et al. *Gene* 234, 109–117, 1999.; Fujishige, K. et al. *J Biol Chem* 274, 18438–18445, 1999.)

Determination of the $IC_{50}$ of cGMP on cAMP PDE Activity of Fractions Pooled from the Center Peak of a 786-O Profile. Fractions were pooled from a 786-O profile from the center peak. Assays were run with cAMP at 0.09 μM substrate. cGMP concentrations were varied to test for inhibition.

Figure 3:
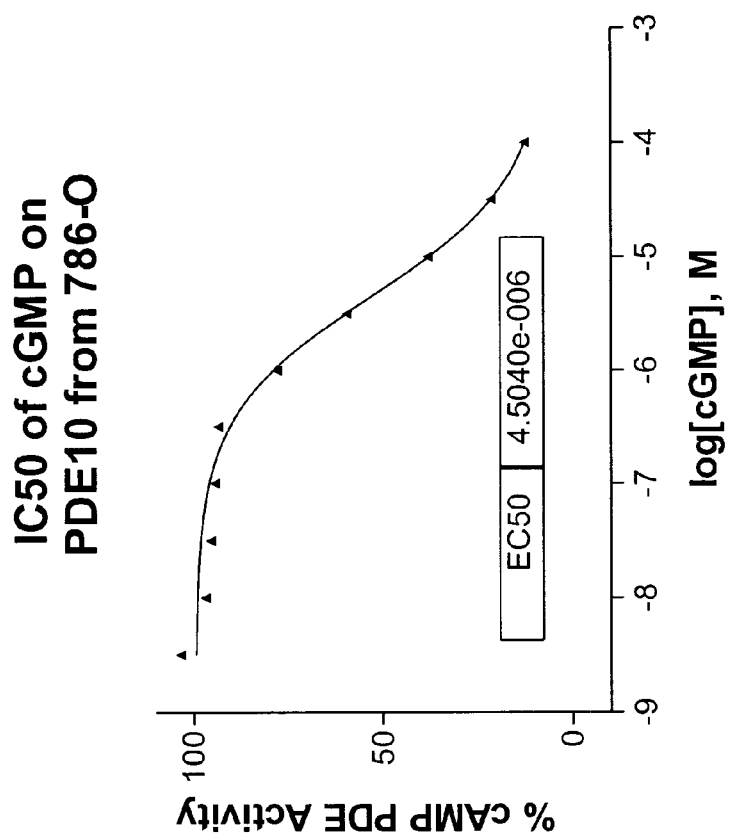
FIG. 3 is a determination of the $IC_{50}$ of cGMP on cAMP PDE activity of fractions pooled from the center peak of a 786-O profile. cGMP inhibited cAMP PDE activity with an $IC_{50}$ of 4.5 μM.

As shown in FIG. 3, cGMP inhibited cAMP PDE activity with an $IC_{50}$ of 4.5 μM. This also shows that the PDE in 786-O has dual substrate specificity for cAMP and cGMP consistent again with PDE10 activity. The $IC_{50}$ of 4.5 μM relative to 0.4 μM for cAMP suggests higher specificity of the enzyme for cAMP than cGMP. The $IC_{50}$ for cGMP inhibition of cAMP PDE is comparable to previous $IC_{50}$'s of cloned and expressed PDE10 of 5.7 and 14 μM (Loughney, K. et al. *Gene* 234, 109–117, 1999.; Fujishige, K. et al. *Eur J Biochem.* 266, 1118–1127, 1999.; Fujishige, K. et al. *J Biol Chem* 274, 18438–18445, 1999.).

Michaelis-Menten Plot (FIG. 4) for cAMP Activity on Fractions Pooled from the Center Peak of a 786-O Profile. cAMP substrate concentrations were varied between 0.01 and 2 μM for 30 min at 30° C. Protein assays were determined using the Bio-Rad DC Protein Assay. A nonlinear regression to the Michalis-Menten equation in Prism was used to determine the $K_m$ and $V_{max}$.

Figure 4:
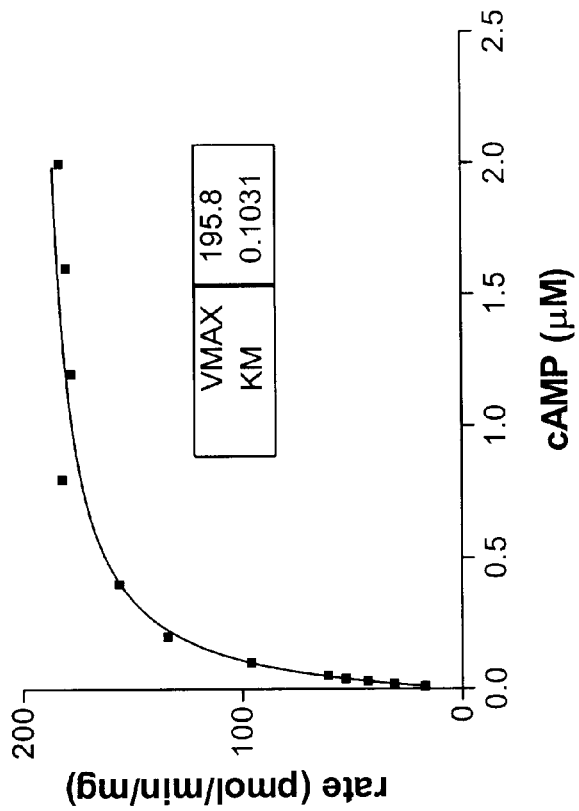
FIG. 4 is a Michaelis-Menten plot for cAMP activity on fractions pooled from the center peak of a 786-O profile. The $K_m$ of cAMP for the 786-O PDE was 0.1 μM which compares to 0.26 μM that was published for a cloned and expressed PDE10 (Fujishige, K. et al. *J Biol Chem* 274, 18438–18445, 1999.).

As shown in FIG. 4, the $K_m$ of cAMP for the 786-O PDE was 0.1 μM which compares to 0.26 μM that was published for a cloned and expressed human PDE10 (Fujishige, K. et al. *J Biol Chem* 274, 18438–18445, 1999.).

Figure 5:
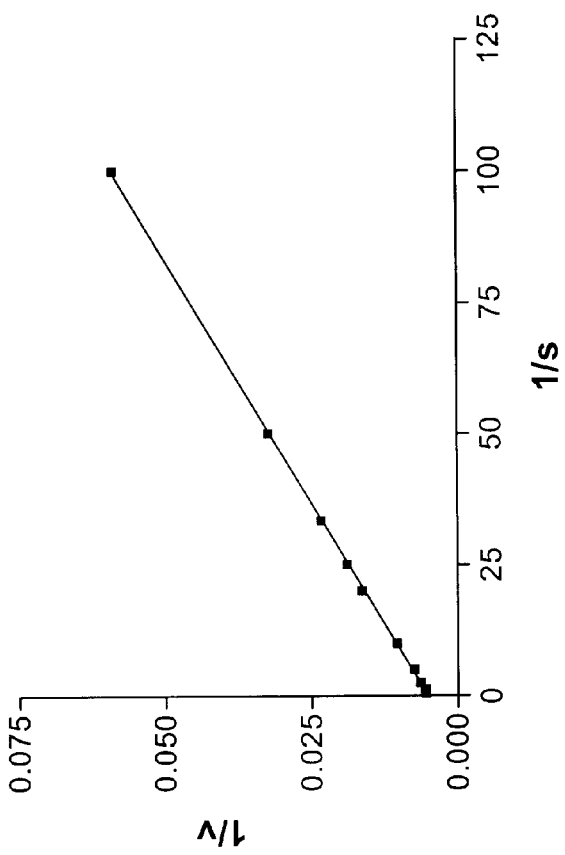
FIG. 5 is a Lineweaver-Burk plot of cAMP activity on fractions pooled from the center peak of a 786-O profile. These data show a linear plot consistent with Michaelis-Menten kinetics, which is characteristic of PDE10 kinetics (Fujishige, K. et al. *J Biol Chem* 274, 18438–18445, 1999.).

Lineweaver-Burk Plot (FIG. 5) of cAMP Activity on Fractions Pooled from the Center Peak of a 786-O Profile. cAMP substrate concentrations were varied between 0.01 and 2 μM for 30 min at 30° C. Data were graphed using 1/rate versus 1/substrate concentration. The line was determnined using a linear regression in Prism.

These data (FIG. 5) show a linear plot consistent with Michaelis-Menten kinetics of this PDE isolated from renal cell carcinoma, which is characteristic of PDE10 kinetics (Fujishige, K. et al. *J Biol Chem* 274, 18438–18445, 1999.).

Michaelis-Menten plot (FIG. 5) for cGMP activity on fractions pooled from the center peak of a 786-O profile. cGMP substrate concentrations were varied between 0.05 and 40 μM for 30 min at 30° C. Protein assays were determined using the Bio-Rad DC Protein Assay. A nonlinear regression to the Michaelis-Menten equation in Prism was used to determine the $K_m$ and $V_{max}$.

Figure 6:
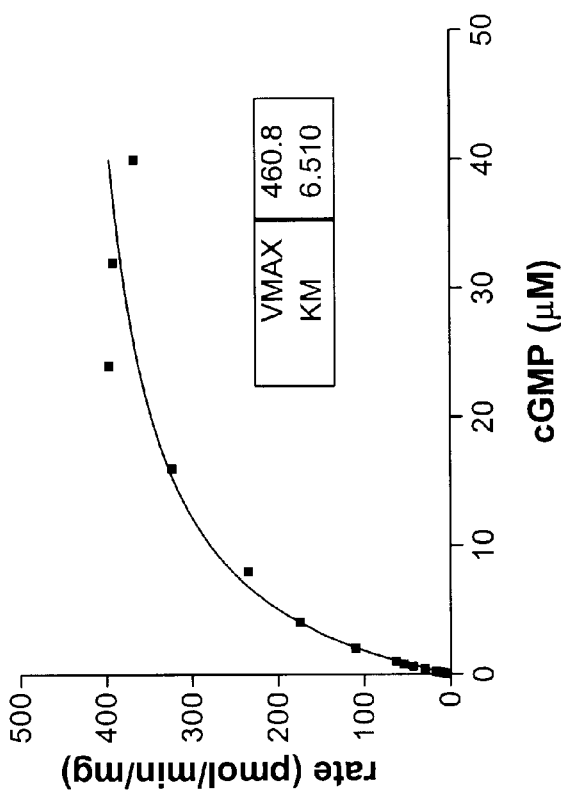
FIG. 6 is a Michaelis-Menten plot for cGMP activity on fractions pooled from the center peak of a 786-O profile. The $K_m$ for cGMP was 6.5 μM which is comparable to previously published values for cloned and expressed PDE10 of 7.2 μM (Fujishige, K. et al. *J Biol Chem* 274, 18438–18445, 1999.).

As shown in FIG. 6, the $K_m$ for cGMP on the PDE enzyme fraction from renal cell carcinoma was 6.5 μM which is comparable to previously published values for cloned and expressed PDE10 of 7.2 μM (Fujishige, K. et al. *J Biol Chem* 274, 18438–18445, 1999.). The $V_{max}$ of 461 pmol/min/mg for cGMP on this fraction was 2.4 times higher than the $V_{max}$ of 196 for cAMP. This $V_{max}$ ratio of cGMP/cAMP is comparable to that seen with a cloned and expressed PDE10 of 2.2 (Fujishige, K. et al. *J Biol Chem* 274, 18438–18445, 1999.).

Figure 7:
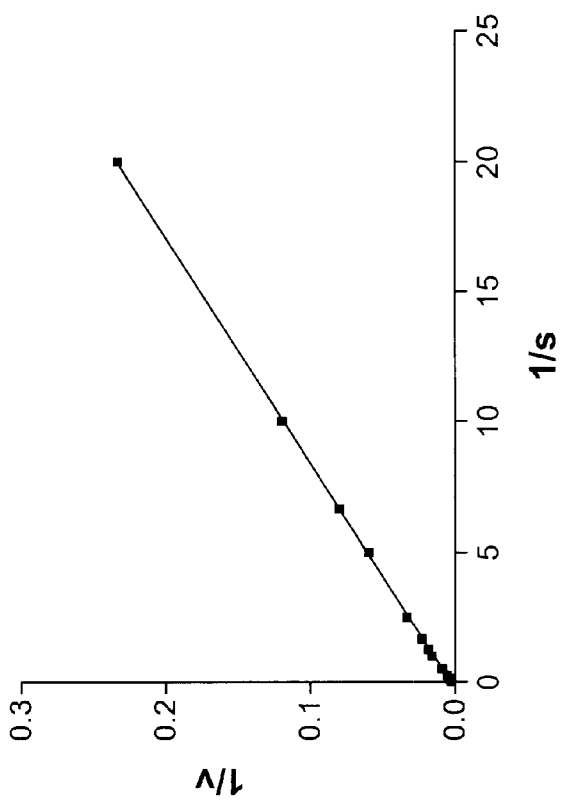
FIG. 7 is a Lineweaver-Burk plot of cGMP activity on fractions pooled from the center peak of a 786-O profile. These data show a linear graph consistent with Michaelis-Menten kinetics, which is characteristic of PDE10 kinetics (Fujishige, K. et al. *J Biol Chem* 274, 18438–18445, 1999.).

Lineweaver-Burk Plot (FIG. 7) of cGMP Activity on Fractions Pooled from the Center Peak of a 786-O Profile. cGMP substrate concentrations were varied between 0.05 and 40 μM for 30 min at 30° C. Data were graphed using 1/rate versus 1/substrate concentration. The line was graphed using a linear regression in Prism.

These data (FIG. 7) show a linear graph consistent with Michaelis-Menten kinetics, which is characteristic of PDE10 kinetics (Fujishige, K. et al. *J Biol Chem* 274, 18438–18445, 1999.).

$IC_{50}$ data (Table 1) on PDE10 from the 786-O renal cell line compared to previously published PDE10 $IC_{50}$ values (Fujishige, K. et al. *J Biol Chem* 274, 18438–18445, 1999.). Km's were determined for pooled fractions 57–75 of PDE10. An average of three values gave a cGMP $K_m$ of 5.5 (1.1) and a cAMP $K_m$ of 0.09 (0.02) (stdev in parenthesis). $IC_{50}$s were determined using the substrate concentrations of 5.5 for cGMP and 0.09 for cAMP.

All of the $IC_{50}$s (Table 1) determined on the PDE10 from 786-O were close to the published $IC_{50}$s determined with a cloned and expressed PDE10 (Fujishige, K. et al. *J Biol Chem* 274, 18438–18445, 1999.).

| Inhibitor | μM $IC_{50}$s on PDE10 from 786-O | | Published $IC_{50}$s on cloned PDE10 | |
| --- | --- | --- | --- | --- |
| | cGMP | cAMP | cGMP | cAMP |
| IBMX | 6.3 | 4.5 | 11 | 17 |
| Zaprinast | 17 | 13 | 14 | 22 |
| Dipyridamole | 0.58 | 0.37 | 0.45 | 1.2 |
| E4021 | 3.2 | 2.8 | 4.2 | 7.2 |
| Vinpocetine | 45 | 38 | 73 | 77 |
| cAMP | 0.43 | | 0.39 | |
| cGMP | | 5.2 | | 14 |
| EHNA | 46 | 60 | >100 | >100 |
| Milrinone | 103 | 84 | >100 | >100 |
| Rolipram | 57 | 40 | >100 | >100 |

EHNA, Milrinone, and Rolipram are N = 1. Others are an average of N = 2.

Realtime RT-PCR. Total RNA was extracted from Sub-confluent renal 786-O cells using Sigma's GenElute Mammalian Total RNA Purification Kit. Realtime RT-PCR was performed using TaqMan Gold RT-PCR kit (AppliedBiosystems, Calif.). In PCR reactions 18S cDNA was used as an internal control to normalize inter-sample variability. The specific primers used for PDE10A1 were 5'GATAGAAGAGAGGAAATCC3'/5'A TTTCTCTACT-GTCTCTGCACTAACACTTT3' and for PDE10A2 were 5'TGCTTCCT GAGCCCCAGTTT3'/5'ATTTCTCTACTGTCTCTGCACTAACACTTT3'. The probe used in both PCR reactions was 6FAMAG-GCATATCTTTCTCTTCACMGBNFQ. PCR was conducted in ABI PRISM® 7000 Sequence Detection System (AppliedBiosystems, CA) according to manufacture's protocols.

Results of Realtime RT-PCR. Realtime PCR data showed that the $\Delta Ct = Ct_{PDE10A1} - Ct_{PDF10A2} = 2.8$ cycles, which indicates that under the current primer condition PDE10A2 transcripts are 6 fold more than PDE10A1 transcripts in 786-O cells, and that PDE10 is present in those cells.

It should be apparent from the above that the cGMP PDE activity isolated from renal cell carcinoma is PDE10.

B. Anti-Neoplastic PDE10 Inhibitors Inhibit Growth of Renal Cell Carcinoma

We have found compounds that inhibit PDE10 that also inhibit growth of renal cell carcinoma cells. In particular compounds of Formula I below represent a class of such inhibitors, one of which (the compound of Example 38 below (hereafter "Compound 38") even has been evaluated in humans and animals for safety, and found to be well tolerated as discussed below. Another compound unexpectedly found to be a PDE10 inhibitor is exisulind, which is also well tolerated in humans. In addition a compound, Compound A (i.e., 1 H-indene-3-acetamide, 5-fluoro-2-methyl-N-(phenylmethyl)-1-[(3,4,5-trimethoxyphenyl)methylene]-, (1Z)) has been found by us to be a PDE 10 inhibitor. Other such compounds are disclosed in U.S. Pat. Nos. 5,401,774, 6,063,818, 5,998,477, and 5,965,619. These patents are incorporated herein by reference.

Figure 8:
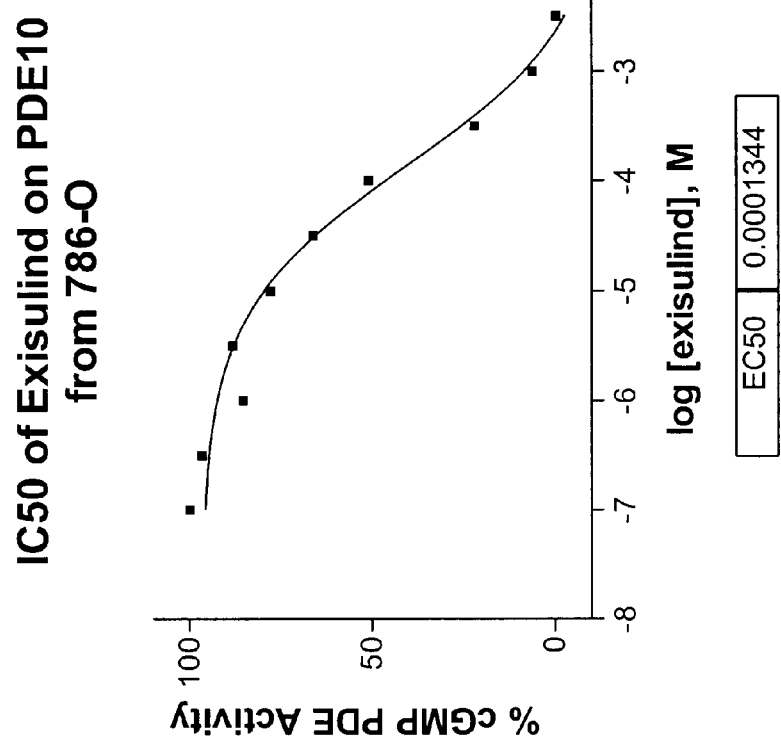
FIG. 8 is an $IC_{50}$ of exisulind on PDE10 from 786-O. Fractions were pooled from the center peak of a 786-O profile. Exisulind showed an $IC_{50}$ of 134 μM on PDE10.

$IC_{50}$ of exisulind on PDE10 from 786-O. Fractions were pooled from the center peak of a 786-O profile. Exisulind concentration was varied to test for inhibition of cGMP PDE activity. As shown in FIG. 8, exisulind showed an $IC_{50}$ of 134 μM on PDE10.

Figure 9:
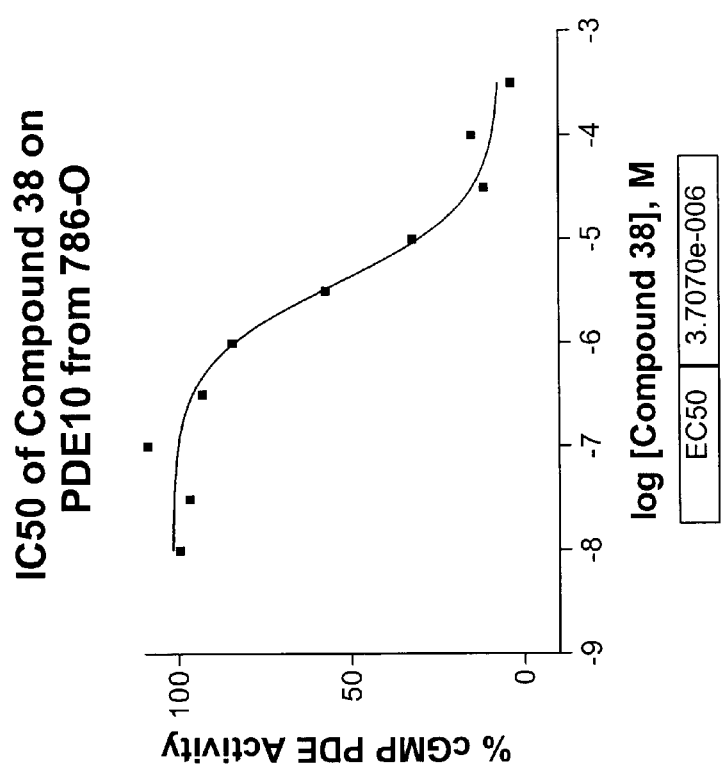
FIG. 9 is an $IC_{50}$ of Compound 38 on PDE10 from 786-O. Compound 38 showed an $IC_{50}$ of 3.7 μM on PDE10.

$IC_{50}$ of Compound 38 on PDE10 Isolated from 786-O. Fractions were pooled from the center peak of a 786-O profile. Compound 38 concentration was varied to test for inhibition of cGMP PDE activity. As shown in FIG. 9, Compound 38 showed an $IC_{50}$ of 3.7 μM on PDE10.

Figure 10:
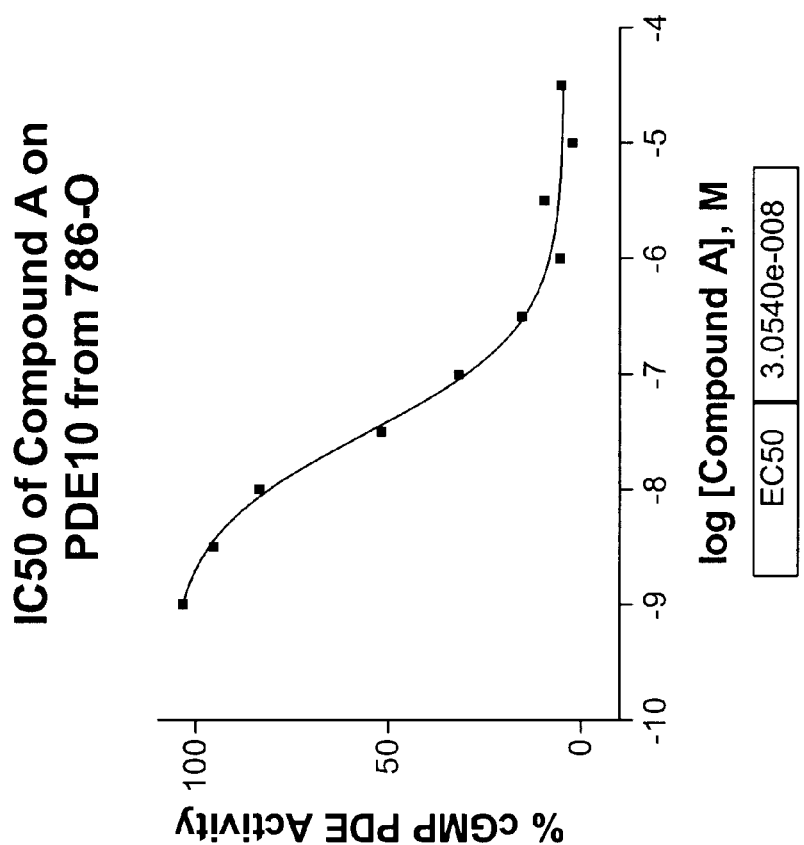
FIG. 10 is an $IC_{50}$ of Compound A on PDE10 from 786-O. Compound A showed an $IC_{50}$ of 31 nM.

$IC_{50}$ of Compound A on PDE10 Isolated from 786-O. Fractions were pooled from the center peak of a 786-O profile. Compound A concentration was varied to test for inhibition of cGMP PDE activity. As shown in FIG. 10, Compound A showed an $IC_{50}$ of 31 nM, a very potent inhibition of the PDE10.

Figure 11:
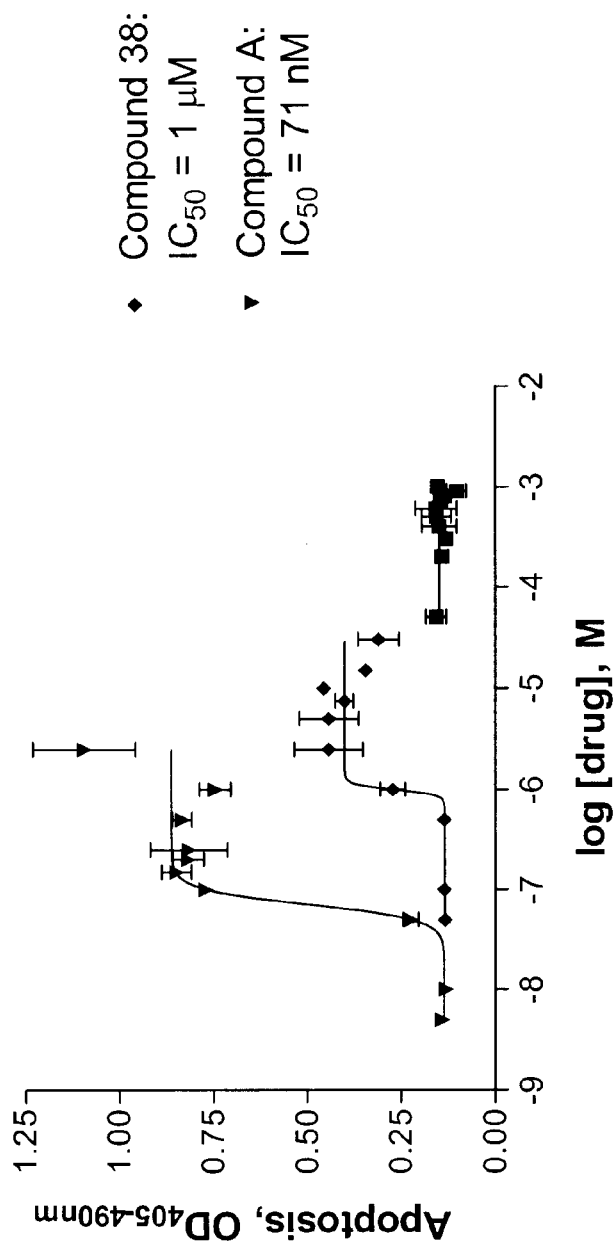
FIG. 11 represents a testing of PDE10-inhibiting compounds for apoptosis on 786-O cells. Compound 38, and Compound A induced apoptosis in the 786-O cell line with $IC_{50}$'s of 1 μM, and 71 nM, respectively.

Testing of PDE10-Inhibiting Compounds for Apoptosis on Renal Carcinoma (786-O) Cells. 10,000 786-O cells per well were plated in RPMI 1640, 1 mM pyruvate, 4.5 g/L glucose, 25 mM Hepes, 5% FCS. After 24 hours, the media was removed and the same media containing the drug was added to the cells (0.1% DMSO final concentration). After 48 hours, apoptosis was detected using the Roche Cell Death Assay. As shown in FIG. 11, Compound 38, and Compound A induced apoptosis in the 786-O cell line with $IC_{50}$'s of 1 μM, and 71 nM, respectively. Exisulind did not show significant induction of apoptosis in the 786-O cells.

Figure 12:
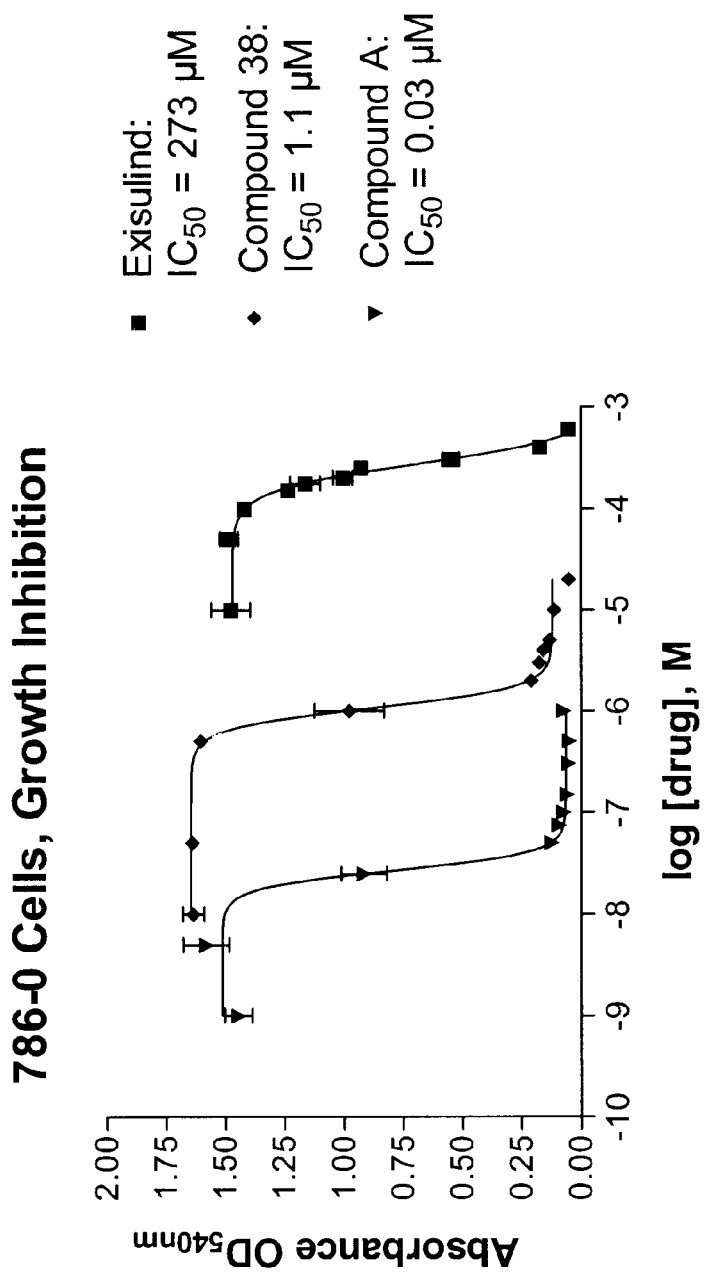
FIG. 12 represents a testing of growth inhibition of PDE10-inhibiting compounds on 786-O. Exisulind, Compound 38, and Compound A inhibited growth of 786-O cells with $IC_{50}$'s of 273 μM, 1.1 μM, and 0.03 μM, respectively.

Testing of Neoplastic Cell Growth Inhibition of PDE10-Inhibiting Compounds on Renal Cell Carcinoma (786-O) Cells. 786-O cells were plated at 1000 cells per well in RPMI 1640, 1 nM pyruvate, 4.5 g/L glucose, 25 mM Hepes, 5% FCS. After 24 hours, the media was removed, and the same media containing the drug was added to the cells (0.1% DMSO final concentration). After 6 days, growth inhibition was determined by staining cells with the sulforhodamine B reagent as previously described (Thompson, W. J. et al. *Adv. Cyclic Nucleotide Res* 10, 69–92, 1979.). As shown in (FIG. 12), exisulind, Compound 38, and Compound A inhibited growth of 786-O cells with $IC_{50}$'s of 273 μM, 1.1 μM, and 0.03 μM, respectively.

Evaluation of biopsies from renal carcinomas also has demonstrated over-expression of cGMP PDE within the malignant cells.

A human clinical study was designed to evaluate the anti-tumor activity of Compound 38 in patients with measurable, locally advanced or metastatic renal cell cancer and to evaluate the safety profile of Compound 38 in this patient population. Patients were treated with 400 mg daily (200 mg twice daily) and continued at this dose throughout the study, provided no intolerable toxicity or disease progression occurred. Disease response was assessed by physical examination, chest x-ray and MRI or CT scan every eight weeks.

Nineteen patients with heavily pre-treated advanced, progressive renal cell carcinoma were entered into the study. An interim evaluation of 16 evaluable patients showed that six had actually achieved stable disease. The patients were on drug daily for a minimum of eight weeks.

No Serious Adverse Event due to the drug was reported in this study. The adverse events, which were reported (regardless of relationship), were of the nature and severity expected in this patient population.

On the basis of these results, our investigators plan to treat 15 additional patients with advanced renal carcinoma with a total daily Compound 38 dose of 800 mg daily (or perhaps higher) po. These patients will have received less extensive prior treatment than the 19 patients who were treated with Compound 38 at 400 mg p.o. daily As can be seen from the above, PDE10 inhibitors are useful in the treatment of renal cell carcinoma.

Compounds of Formula I below (as well as their pharmaceutically acceptable salts) include PDE10 inhibitors:

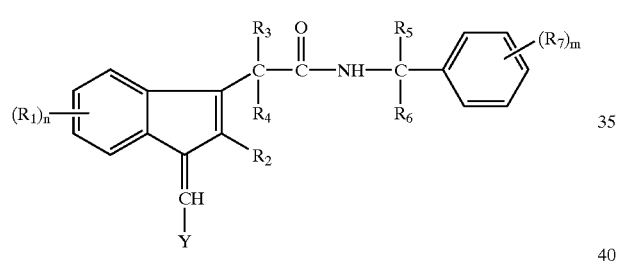

I wherein $R_1$ is independently selected in each instance from the group consisting of hydrogen, halogen, lower alkyl, lower alkoxy, amino, lower alkylamino, di-lower alkylamino, lower alkylmercapto, lower alkyl sulfonyl, cyano, carboxamide, carboxylic acid, mercapto, sulfonic acid, xanthate and hydroxy;

$R_2$ is selected from the group consisting of hydrogen and lower alkyl;

$R_3$ is selected from the group consisting of hydrogen, halogen, amino, hydroxy, lower alkyl amino, and di-loweralkylamino;

$R_4$ is hydrogen, or $R_3$ and $R_4$ together are oxygen;

$R_5$ and $R_6$ are independently selected from the group consisting of hydrogen, lower alkyl, hydroxy-substituted lower alkyl, amino lower alkyl, lower alkylamino-lower alkyl, lower alkyl amino di-lower alkyl, lower alkyl nitrile, —$CO_2H$, —$C(O)NH_2$, and a $C_2$ to $C_6$ amino acid;

$R_7$ is independently selected in each instance from the group consisting of hydrogen, amino lower alkyl, lower alkoxy, lower alkyl, hydroxy, amino, lower alkyl amino, di-lower alkyl amino, halogen, —$CO_2H$, —$SO_3H$, —$SO_2NH_2$, and —$SO_2$(lower alkyl);

m and n are integers from 0 to 3 independently selected from one another;

Y is selected from the group consisting of quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or substituted variants thereof wherein the substituents are one or two selected from the group consisting of halogen, lower alkyl, lower alkoxy, amino, lower alkylamino, di-lower alkylamino, hydroxy, —$SO_2$(lower alkyl) and —$SO_2NH_2$.

Preferred compounds of this invention for use with the methods described herein include those of Formula I where:

$R_1$ is selected from the group consisting of halogen, lower alkoxy, amino, hydroxy, lower alkylamino and di-loweralkylamino, preferably halogen, lower alkoxy, amino and hydroxy;

$R_2$ is lower alkyl;

$R_3$ is selected from the group consisting of hydrogen, halogen, hydroxy, amino, lower alkylamino and di-loweralkylamino, preferably, hydrogen, hydroxy and lower alkylamino;

$R_5$ and $R_6$ are independently selected from the group consisting of hydrogen, hydroxy-substituted lower alkyl, amino lower alkyl, lower alkylamino-lower alkyl, lower alkyl amino di-lower alkyl, —$CO_2H$, —$C(O)NH_2$; preferably hydrogen, hydroxy-substituted lower alkyl, lower alkyl amino di-lower alkyl, —$CO_2H$, and —$C(O)NH_2$;

$R_7$ is independently selected in each instance from the group consisting of hydrogen, lower alkoxy, hydroxy, amino, lower alkyl amino, di-lower alkyl amino, halogen, —$CO_2H$, —$SO_3H$, —$SO_2NH_2$, and —$SO_2$ (lower alkyl); preferably hydrogen, lower alkoxy, hydroxy, amino, amino lower alkyl, halogen, —$CO_2H$, —$SO_3H$, —$SO_2NH_2$, and —$SO_2$(lower alkyl);

Preferably, at least one of the $R_7$ substituents is para- or ortho-located; most preferably ortho-located;

Y is selected from the group consisting of quinolinyl, isoquinolinyl, pyridinyl, pyrimidinyl and pyrazinyl or said substituted variants thereof.

Preferably, the substituents on Y are one or two selected from the group consisting of lower alkoxy, amino, lower alkylamino, di-lower alkylamino, hydroxy, —$SO_2$(lower alkyl) and —$SO_2NH_2$; most preferably lower alkoxy, di-lower alkylamino, hydroxy, —$SO_2$(lower alkyl) and —$SO_2NH_2$.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "hydroxy-substituted lower alkyl" refers to lower alkyl groups that are substituted with at least one hydroxy group, preferably no more than three hydroxy groups.

The term "—$SO_2$(lower alkyl)" refers to a sulfonyl group that is substituted with a lower alkyl group.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional crystallization of diastereomeric salts and the like.

Compounds of Formula I also can exist as geometrical isomers (Z and E); the Z isomer is preferred.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The compounds of this invention can be formulated with pharmaceutically acceptable carriers into unit dosage forms in a conventional manner so that the patient in need of therapy can periodically (e.g., once or more per day) take a compound according to the methods of this invention. The exact initial dose of the compounds of this invention can be determined with reasonable experimentation. The initial dosage calculation would also take into consideration several factors, such as the formulation and mode of administration, e.g. oral or intravenous, of the particular compound. A total daily oral dosage of about 50 mg–2.0 gr of such compounds would achieve a desired systemic circulatory concentration. As discussed above and below, an oral dose of about 400–1600 mg/day is appropriate in mammals.

Preferably, the treatment of mammalian cells in need of PDE10 inhibition with a compound of this invention should be continuous over an extended period of time. By continuous, we do not mean to suggest that drug be present or taken all the time. We mean that it be present most of the time at levels sufficient to cause neoplastic cell death.

The pharmaceutical compositions of this invention are preferably packaged in a container (e.g., a box or bottle, or both) with suitable printed material (e.g., a package insert) containing indications and directions for use in the treatment of a disease where GSK3 inhibition is desired, etc.

There are several general schemes for producing compounds of Formula I useful in this invention. One general scheme (which has several sub-variations) involves the case where both $R_3$ and R4 are both hydrogen. This first scheme is described immediately below in Scheme I. The other general scheme (which also has several sub-variations) involves the case where at least one of $R_3$ and $R_4$ is a moiety other than hydrogen but within the scope of Formula I above. This second scheme is described below as "Scheme II."

The general scheme for preparing compounds where both $R_3$ and $R_4$ are both hydrogen is illustrated in Scheme I, which is described in part in U.S. Pat. No. 3,312,730, which is incorporated herein by reference. In Scheme I, $R_1$ is as defined in Formula I above. However, in Scheme I, that substituent can also be a reactive moiety (e.g. a nitro group) that later can be reacted to make a large number of other substituted indenes from the nitro-substituted indenes.

Scheme I
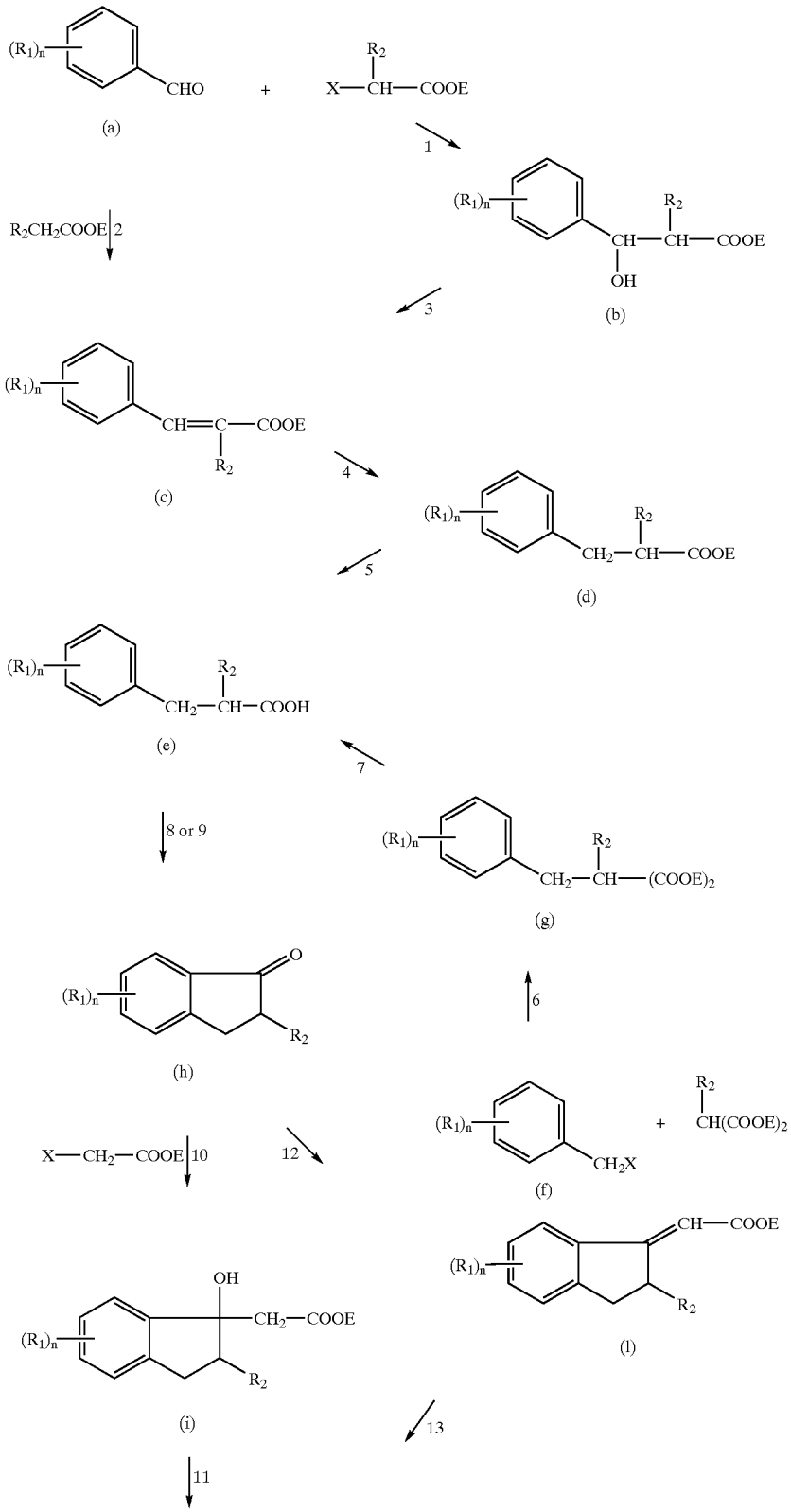

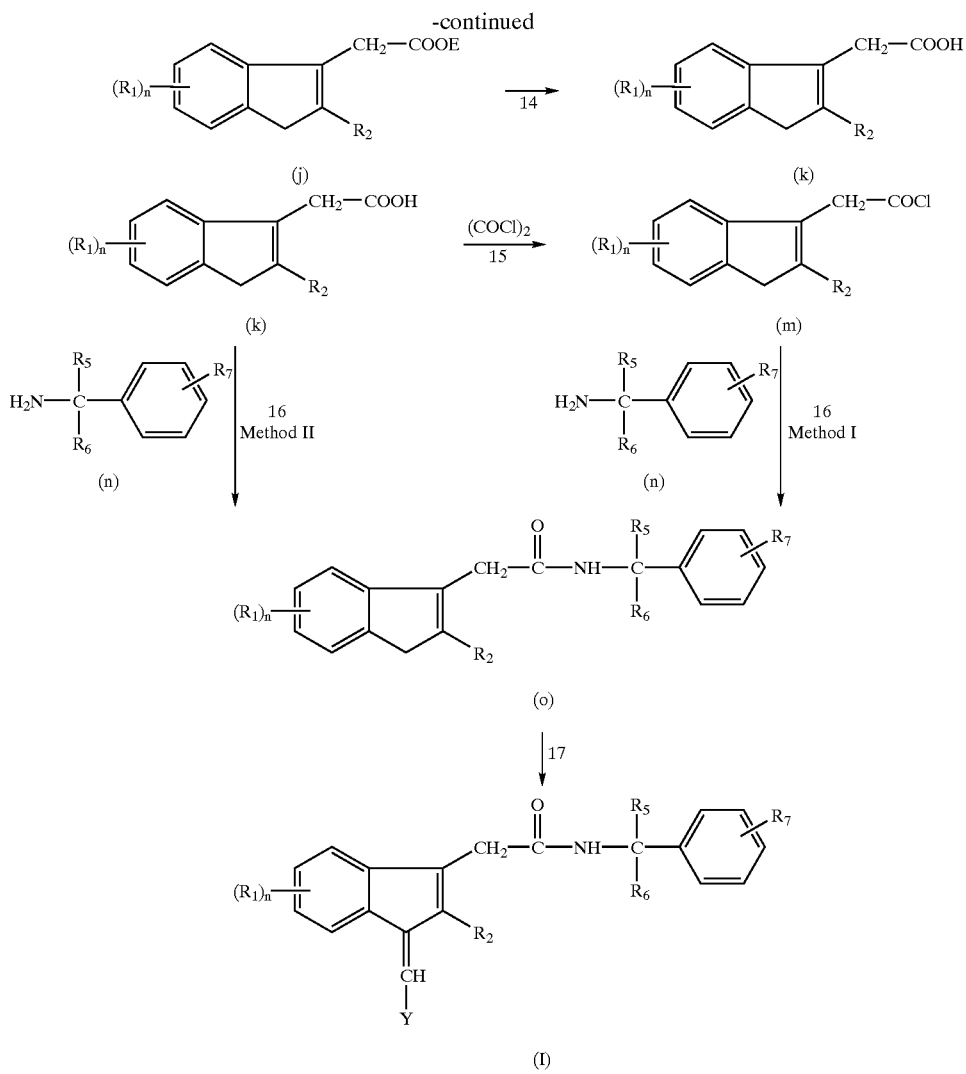

In Scheme I, several sub-variations can be used. In one sub-variation, a substituted benzaldehyde (a) may be condensed with a substituted acetic ester in a Knoevenagel reaction (see reaction 2) or with an α-halogeno propionic ester in a Reformatsky Reaction (see reactions 1 and 3). The resulting unsaturated ester (c) is hydrogenated and hydrolyzed to give a substituted benzyl propionic acid (e) (see reactions 4 and 5). Alternatively, a substituted malonic ester in a typical malonic ester synthesis (see reactions 6 and 7) and hydrolysis decarboxylation of the resulting substituted ester (g) yields the benzyl propionic acid (e) directly. This latter method is especially preferable for nitro and alkylthio substituents on the benzene ring.

The next step is the ring closure of the β-aryl proponic acid (e) to form an indanone (h) which may be carried out by a Friedel-Crafts Reaction using a Lewis acid catalyst (Cf. Organic Reactions, Vol. 2, p. 130) or by heating with polyphosphoric acid (see reactions 8 and 9, respectively). The indanone (h) may be condensed with an α-halo ester in the Reformatsky Reaction to introduce the aliphatic acid side chain by replacing the carboxyl group (see reaction 10). Alternately, this introduction can be carried out by the use of a Wittig Reaction in which the reagent is a α-triphenylphosphinyl ester, a reagent that replaces the carbonyl with a double bond to the carbon (see reaction 12). This product (1) is then immediately rearranged into the indene 0)(see reaction 13). If the Reformatsky Reaction route is used, the intermediate 3-hydroxy-3-aliphatic acid derivative i must be dehydrated to the indene (j) (see reaction 11).

The indenylacetic acid (k) in THF then is allowed to react with oxalyl or thionyl chloride or similar reagent to produce the acid chloride (m) (see reaction 15), whereupon the solvent is evaporated. There are two methods to carry out reaction 16, which is the addition of the benzylamine side chain (n).

Method (I)

In the first method, the benzylamine (n) is added slowly at room temperature to a solution of 5-fluoro-2-methyl-3-indenylacetyl chloride in $CH_2Cl_2$. The reaction mixture is refluxed overnight, and extracted with aqueous HCl (10%), water, and aqueous $NaHCO_3$ (5%). The organic phase is dried ($Na_2SO_4$) and is evaporated to give the amide compound (o).

Method (II)

In the second method, the indenylacetic acid (k) in DMA is allowed to react with a carbodiimide (e.g. N-(3- dimethylaminopropyl)-N'-ethylcarbodiimide hydrochloride) and benzylamine at room temperature for two days. The reaction mixture is added dropwise to stirred ice water. A yellow precipitate is filtered off, is washed with water, and is dried in vacuo. Recrystallization gives the amide compound (o).

Compounds of the type a' (Scheme III), o (Scheme I), t (Scheme II), y (Scheme IIB) may all be used in the condensation reaction shown in Scheme III.

Substituents

X=halogen, usually Cl or Br.

E=methyl, ethyl or benzyl, or lower acyl.

$R_1$, $R_2$, $R_6$, $R_5$, and $R_7$=as defined in Formula I.

Y, n and m=as defined in Formula I.

Reagents and general conditions for Scheme I (numbers refer to the numbered reactions):

(1) Zn dust in anhydrous inert solvent such as benzene and ether.
(2) $KHSO_4$ or p-toluene sulfonic acid.
(3) $NaOC_2H_5$ in anhydrous ethanol at room temperature.
(4) $H_2$ palladium on charcoal, 40 p.s.i. room temperature.
(5) NaOH in aqueous alcohol at 20–100°.
(6) $NaOC_2H_5$ or any other strong base such as NaH or K-t-butoxide.
(7) Acid.
(8) Friedel-Crafts Reaction using a Lewis Acid catalyst Cf. Organic Reactions, Vol. II, p. 130.
(9) Heat with polyphosphoric acid.
(10) Reformatsky Reaction: Zn in inert solvent, heat.
(11) p-Toluene sulfonic acid and $CaCl_2$ or $I_2$ at 200°
(12) Wittig Reaction using $(C_6H_5)_3$ P=C—COOE 20–80° in ether or benzene
(13) (a) $NBS/CCl_4$/benzoyl peroxide (b) $PtO_2$/ $H_2$ (1 atm.)/acetic acid
(14) (a) NaOH (b) HCl
(15) Oxalyl or thionyl chloride in $CH_2Cl_2$ or THF
(16) Method I: 2 equivalents of $NH_2$—$C(R_5R_6)$—Ph—$(R_7)_m$ Method II: carbodiimide in THF
(17) IN $NaOCH_3$ in MeOH under reflux conditions Indanones within the scope of compound (h) in Scheme I are known in the literature and are thus readily available as intermediates for the remainder of the synthesis so that reactions 1–7 can be conveniently avoided. Among such known indanones are:

5-methoxyindanone 6-methoxyindanone 5-methylindanone 5-methyl-6-methoxyindanone 5-methyl-7-chloroindanone 4-methoxy-7-chloroindanone 4-isopropyl-2,7-dimethylindanone 5,6,7-trichloroindanone 2-n-butylindanone 5-methylthioindanone Scheme II has two mutually exclusive sub-schemes: Scheme IIA and Scheme II B. Scheme II A is used when $R_3$ is hydroxy and $R_4$ is hydrogen or when the two substituents form an oxo group. When $R_3$ is lower alkyl amino, Scheme II B is employed.

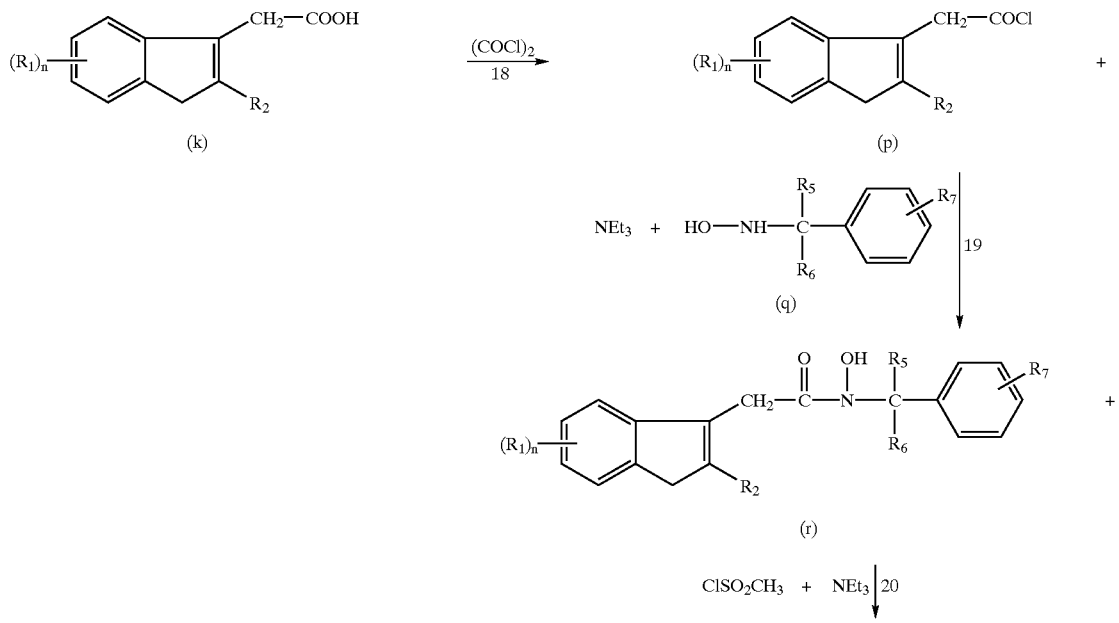

Scheme IIA

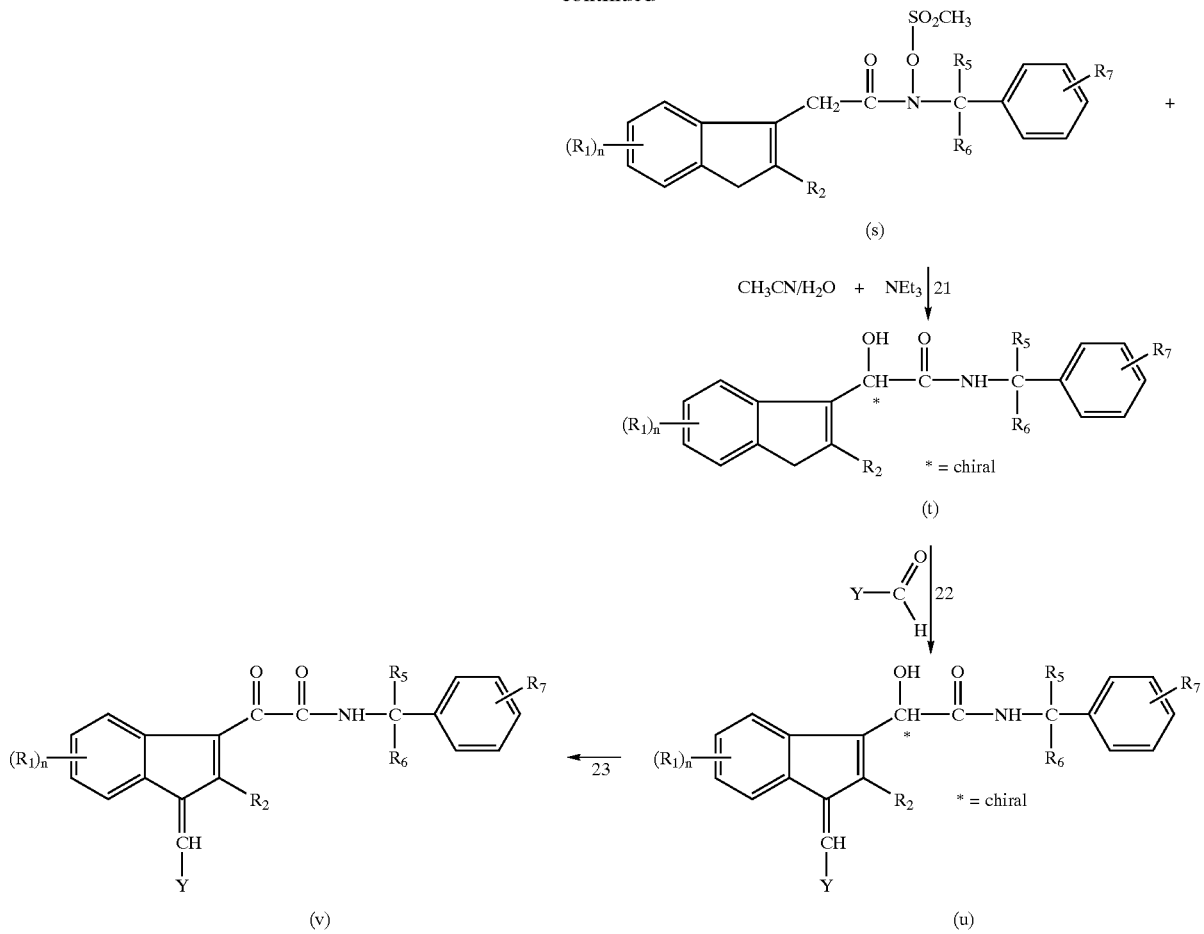

Similar to Scheme I, in Scheme IIA the indenylacetic acid (k) in THF is allowed to react with oxalylchloride under reflux conditions to produce the acid chloride (p) (see reaction 18), whereupon the solvent is evaporated. In reaction 19, a 0° C. mixture of a benzyl hydroxylamine hydrochloride (q) and $Et_3N$ is treated with a cold solution of the acid chloride in $CH_2Cl_2$ over a period of 45–60 minutes. The mixture is warmed to room temperature and stirred for one hour, and is treated with water. The resulting organic layer is washed with 1 N HCl and brine, is dried over magnesium sulfate and is evaporated. The crude product, a N-hydroxy-N-benzyl acetamide (r) is purified by crystallization or flash chromatography. This general procedure is taught by Hoffman et al., JOC 1992, 57, 5700–5707.

The next step is the preparation of the N-mesyloxy amide (s) in reaction 20, which is also taught by Hoffman et al., JOC 1992, 57, 5700–5707. Specifically, to a solution of the hydroxamic acid (r) in $CH_2Cl_2$ at 0° C. is added triethylamine. The mixture is stirred for 10–12 minutes, and methanesulfonyl chloride is added dropwise. The mixture is stirred at 0° C. for two hours, is allowed to warm to room temperature, and is stirred for another two hours. The organic layer is washed with water, 1 N HCl, and brine, and is dried over magnesium sulfate. After rotary evaporation, the product(s) is usually purified by crystallization or flash chromatography.

The preparation of the N-benzyl-α-(hydroxy) amide (t) in reaction 21, is also taught by Hoffman et al., JOC 1992, 57, 5700–5707 and Hoffman et al., JOC 1995, 60, 4121–4125. Specifically, to a solution of the N-(mesyloxy) amide (s) in $CH_3CN/H_2O$ is added triethylamine in $CH_3CN$ over a period of 6–12 hours. The mixture is stirred overnight. The solvent is removed, and the residue is dissolved in ethyl acetate. The solution is washed with water, 1 N HCl, and brine, and is dried over magnesium sulfate. After rotary evaporation, the product (t) is usually purified by recrystallization.

Reaction 22 in Scheme IIA involves a condensation with certain aldehydes, which is described in Scheme III below, a scheme that is common to products made in accordance with Schemes I, IIA and IIB.

The final reaction 23 in Scheme IIA is the preparation of the N-benzyl-α-ketoamide (v), which involves the oxidation of a secondary alcohol (u) to a ketone by e.g., a Pfitzner-Moffatt oxidation, which selectively oxidizes the alcohol without oxidizing the Y group. Compounds (u) and (v) may be derivatized to obtain compounds with $R_3$ and $R_4$ groups as set forth in Formula 1.

As explained above, Scheme IIB is employed when $R_3$ is lower alkyl amino.

Scheme IIB

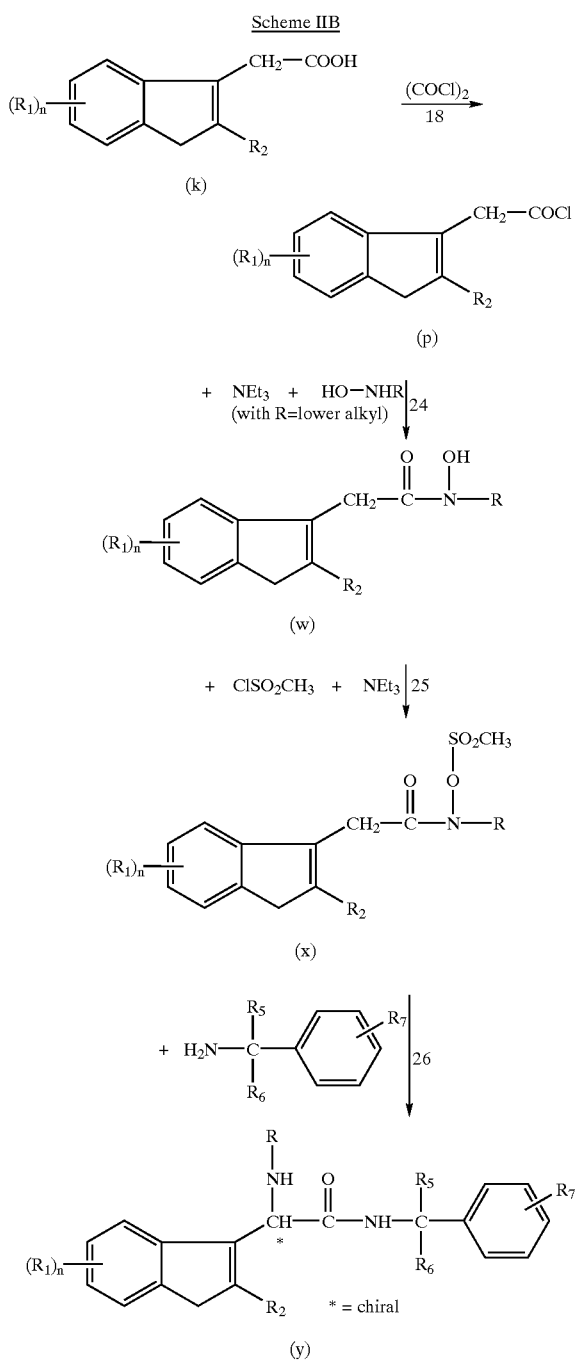

Scheme III

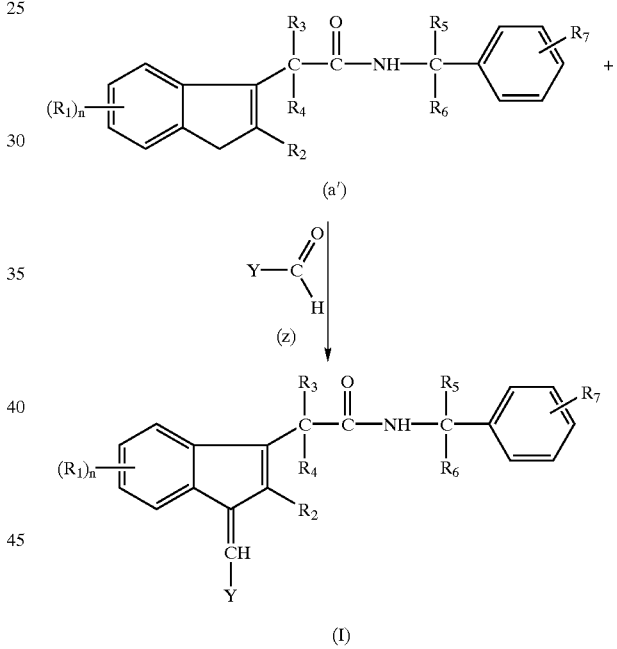

Similar to Scheme I, in Scheme IIB the indenylacetic acid (k) in THF is allowed to react with oxalylchloride under reflux conditions to produce the acid chloride (p) (see reaction 18), whereupon the solvent is evaporated. In reaction 24, a mixture of an alkyl hydroxylamine hydrochloride (i.e. HO—NHR where R is a lower alkyl, preferably isopropyl) and $Et_3N$ is treated at 0° C. with a cold solution of the acid chloride in $CH_2Cl_2$ over a period of 45–60 minutes. The mixture is warmed to room temperature and is stirred for one hour, and is diluted with water. The resulting organic layer is washed with 1 N HCl and brine, is dried over magnesium sulfate and is evaporated. The crude product, a N-hydroxy-N-alkyl acetamide (w) is purified by crystallization or flash chromatography. This general procedure is also taught by Hoffman et al., JOC 1992, 57, 5700–5707

The preparation of the N-mesyloxy amide (x) in reaction 25, which is also taught by Hoffman et al., JOC 1992, 57, 5700–5707. Specifically, a solution of the hydroxamic acid (w) in $CH_2Cl_2$ at 0° C. is treated with triethylamine, is stirred for 10–12 minutes, and is treated dropwise with methanesulfonyl chloride. The mixture is stirred at 0° C. for two hours, is allowed to warm to room temperature, and is stirred for another two hours. The resulting organic layer is washed with water, 1 N HCl, and brine, and is dried over magnesium sulfate. After rotary evaporation, the product (x) is usually purified by crystallization or flash chromatography.

The preparation of the N-benzyl indenyl-α-loweralkylamino- acetamide compound (y) in Scheme IIB as taught by Hoffman et al., JOC 1995, 60, 4121–25 and J. Am. Chem Soc. 1993, 115, 5031–34, involves the reaction of the N-mesyloxy amide (x), with a benzylamine in $CH_2Cl_2$ at 0° C. is added over a period of 30 minutes. The resulting solution is stirred at 0° C. for one hour and at room temperature overnight. The solvent is removed, and the residue is treated with 1 N NaOH. The extract with $CH_2Cl_2$ is washed with water and is dried over magnesium sulfate. After rotary evaporation, the product (y) is purified by flash chromatography or crystallization.

Scheme III involves the condensation of the heterocycloaldehydes (i.e., y—CHO) with the indenyl amides to produce the final compounds of Formula I. This condensation is employed, for example, in reaction 17 in Scheme I above and in reaction 22 in Scheme IIA. It is also used to convert compound (y) in Scheme IIB to final compounds of Formula I.

In Scheme III, the amide (a') from the above schemes, an N-heterocycloaldehyde (z), and sodium methoxide (1 M in methanol) are stirred at 60° C. under nitrogen for 24 hours. After cooling, the reaction mixture is poured into ice water. A solid is filtered off, is washed with water, and is dried in vacuo. Recrystallization provides a compound of Formula I in Schemes I and IIB and the intermediate (u) in Scheme IIA.

As has been pointed out above, it is preferable in the preparation of many types of the compounds of this invention, to use a nitro substituent on the benzene ring of the indanone nucleus and convert it later to a desired substituent since by this route a great many substituents can be reached. This is done by reduction of the nitro to the amino group followed by use of the Sandmeyer reaction to introduce chlorine, bromine, cyano or xanthate in place of the amino. From the cyano derivatives, hydrolysis yields the carboxamide and carboxylic acid; other derivatives of the carboxy group such as the esters can then be prepared. The xanthates, by hydrolysis, yield the mercapto group that may be oxidized readily to the sulfonic acid or alkylated to an alkylthio group that can then be oxidized to alkylsulfonyl groups. These reactions may be carried out either before or after the introduction of the 1-substituent.

The foregoing may be better understood from the following examples that are presented for purposes of illustration and are not intended to limit the scope of the invention. As used in the following examples, the references to substituents such as $R_1$, $R_2$, etc., refer to the corresponding compounds and substituents in Formula I above.

EXAMPLE 1

(Z)-5-Fluoro-2-methyl-(4-pyridinylidene)-3-(N-benzyl)-indenylacetamide (A) p-Fluoro-α-methylcinnamic Acid p-Fluorobenzaldehyde (200 g, 1.61 mol), propionic anhydride (3.5 g, 2.42 mol) and sodium propionate (155 g, 1.61 mol) are mixed in a one liter three-necked flask which had been flushed with nitrogen. The flask is heated gradually in an oil-bath to 140° C. After 20 hours, the flask is cooled to 100° C. and poured into 8 l of water. The precipitate is dissolved by adding potassium hydroxide (302 g) in 2 l of water. The aqueous solution is extracted with ether, and the ether extracts are washed with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic Acid

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the solvent is evaporated in vacuo to give the product, p-fluoro-α-methylhydrocinnamic acid, which was used directly in the next step.

(C) 6-Fluoro-2-methylindanone

To 932 g polyphosphoric acid at 70° C. (steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and is added to 2 l. of water. The aqueous suspension is extracted with ether. The extract is washed twice with saturated sodium chloride solution, 5% $Na_2CO_3$ solution, and water, and is dried, and is concentrated on 200 g silica-gel; the slurry is added to a five pound silica-gel column packed with 5% ether-petroleum ether. The column is eluted with 5–10% ether-petroleum ether, to give 6-fluoro-2-methylindanone. Elution is followed by TLC.

(D) 5-Fluoro-2-methylindenyl-3-acetic Acid

A mixture of 6-fluoro-2-methylindanone (18.4 g, 0.112 mol), cyanoacetic acid (10.5 g, 0.123 mol), acetic acid (6.6 g), and ammonium acetate (1.7 g) in dry toluene (15.5 ml) is refluxed with stirring for 21 hours, as the liberated water is collected in a Dean Stark trap. The toluene is evaporated, and the residue is dissolved in 60 ml of hot ethanol and 14 ml of 2.2 N aqueous potassium hydroxide solution. 22 g of 85% KOH in 150 ml of water is added, and the mixture refluxed for 13 hours under nitrogen. The ethanol is removed under vacuum, and 500 ml water is added. The aqueous solution is extracted well with ether, and is then boiled with charcoal. The aqueous filtrate is acidified to pH 2 with 50% cold hydrochloric acid. The precipitate is dried and 5-fluoro-2-methylindenyl-3-acetic acid (M.P. 164–166° C.) is obtained.

(E) 5-Fluoro-2-methylindenyl-3-acetyl Chloride 5-fluoro-2-methylindenyl-3-acetic acid (70 mmol) in THF (70 ml) is allowed to react with oxalylchloride (2 M in $CH_2Cl_2$; 35 ml; 70 mmol) under reflux conditions (24 hours). The solvent is evaporated to yield the title compound, which is used as such in the next step.

(F) 5-Fluoro-2-methyl-3-(N-benzyl)-indenylacetamide

Benzylamine (5 mmol) is added slowly at room temperature to a solution of 5-fluoro-2-methylindenyl-3-acetyl chloride (2.5 mmol.) in $CH_2Cl_2$ (10 ml). The reaction mixture is refluxed overnight, and is extracted with aqueous HCl (10%), water, and aqueous $NaHCO_3$ (5%). The organic phase is dried ($Na_2SO_4$) and is evaporated to give the title compound, which is recrystallized from $CH_2Cl_2$ to give the title compound as a white solid (m.p. 144° C.).

(G) (Z)-5-Fluoro-2-methyl-(4-pyridinylidene)-3-(N-benzyl)-indenylacetamide 5-fluoro-2-methyl-3-(N-benzyl)-indenylacetamide (3.38 mmol), 4-pyridinecarboxaldehyde (4 mmol), sodium methoxide (1M $NaOCH_3$ in methanol (30 ml)) are heated at 60° C. under nitrogen with stirring for 24 hours. After cooling, the reaction mixture is poured into ice water (200 ml). A solid is filtered off, washed with water, and dried in vacuo. Recrystallization from $CH_3CN$ gives the title compound (m.p. 202° C.) as a yellow solid($R_1$=F,$R_2$=$CH_3$, $R_3$=H, $R_4$=H, $R_5$=H, $R_6$=H, $R_7$=H, n=1, m=1, Y=4-pyridinyl).

(H) (E)-5-Fluoro-2-methyl-(4-pyridinylidene)-3-(N-benzyl)-indenylacetamide

The mother liquor obtained from the $CH_3CN$ recrystallization of 1 G is rich on the geometrical isomer of 1G. The E-isomer can be obtained pure by repeated recrystallizations from $CH_3CN$.

EXAMPLE 2

(Z)-5-Fluoro-2-methyl-(3-pyridinylidene)-3-(N-benzyl)-indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 3-pyridinecarboxaldehyde. Recrystallization from $CH_3CN$ gives the title compound (m.p. 175° C.)($R_1$=F, $R_2$=$CH_3$, $R_3$=H, $R_4$=H, $R_5$=H, $R_6$=H, $R_7$=H, n=1, m=1, Y=3-pyridinyl).

EXAMPLE 3

(Z)-5-Fluoro-2-methyl-(2-pyridinylidene)-3-(N-benzyl)-indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 2-pyridinecarboxaldehyde.

Recrystallization from ethylacetate gives the title compound (m.p. 218° C.)($R_1$=F, $R_2$=$CH_3$, $R_3$=H, $R_4$=H, $R_5$=H, $R_6$=H, $R_7$=H, n=1, m=1, Y=2-pyridinyl).

EXAMPLE 4

(Z)-5-Fluoro-2-methyl-(4-quinolinylidene)-3-(N-benzyl)-indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 4-quinolinecarboxaldehyde. Recrystallization from ethylacetate gives the title compound (m.p. 239° C.)($R_1$=F, $R_2$=$CH_3$, $R_3$=H, $R_4$=H, $R_5$=H, $R_6$=H, $R_7$=H, n=1, m=1, Y=4-quinolinyl).

EXAMPLE 5

(Z)-5-Fluoro-2-methyl-(4,6-dimethyl-2-pyridinylidene)-3-(N-benzyl)-indenylacetamide 5-Fluoro-2-methyl-3-(N-benzyl)-indenylacetamide from Example 1, part F is allowed to react with 4,6-dimethyl-2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, Y=4,6-dimethyl-2-pyridinyl).

EXAMPLE 6

(Z)-5-Fluoro-2-methyl-(3-quinolinylidene)-3-(N-benzyl)-indenylacetamide

5-Fluoro-2-methyl-3-(N-benzyl)-indenylacetamide from Example 1, part F is allowed to react with 3-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-quinolinyl).

EXAMPLE 7

(Z)-5-Fluoro-2-methyl-(2-quinolinylidene)-3-(N-benzyl)-indenylacetamide

5-Fluoro-2-methyl-3-(N-benzyl)-indenylacetamide from Example 1, part F is allowed to react with 2-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-quinolinyl).

EXAMPLE 8

(Z)-5-Fluoro-2-methyl-(Pyridinylidene)-3-(N-benzyl)-indenylacetamide

5-Fluoro-2-methyl-3-(N-benzyl)-indenylacetamide from Example 1, part F is allowed to react with pyrazinealdehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=pyrazinyl).

EXAMPLE 9

(Z)-5-Fluoro-2-methyl-(3-pyridazinylidene)-3-(N-benzyl)-indenylacetamide

5-Fluoro-2-methyl-3-(N-benzyl)-indenylacetamide from Example 1, part F is allowed to react with pyridazine-3-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-pyridazinyl).

EXAMPLE 10

(Z)-5-Fluoro-2-methyl-(4-pyrimidinylidene)-3-(N-benzyl)-indenylacetamide

5-Fluoro-2-methyl-3-(N-benzyl)-indenylacetamide from Example 1, part F is allowed to react with pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyrimidinyl).

EXAMPLE 11

(Z)-5-Fluoro-2-methyl-(2-methyl-4-pyrimidinylidene)-3-(N-benzyl)-indenylacetamide 5-Fluoro-2-methyl-3-(N-benzyl)-indenylacetamide from Example 1, part F is allowed to react with 2-methyl-pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-pynmidinyl).

EXAMPLE 12

(Z)-5-Fluoro-2-methyl-(4-pyridazinylidene)-3-(N-benzyl)-indenylacetamide

5-Fluoro-2-methyl-3-(N-benzyl)-indenylacetamide from Example 1, part F is allowed to react with pyridazine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyridazinyl).

EXAMPLE 13

(Z)-5-Fluoro-2-methyl-(1-methyl-3-indolylidene)-3-(N-benzyl)-indenylacetamide

5-Fluoro-2-methyl-3-(N-benzyl)-indenylacetamide from Example 1, part F is allowed to react with 1-methylindole-3-carboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-methyl-3-indoly).

EXAMPLE 14

(Z)-5-Fluoro-2-methyl-(1-acetyl-3-indolylidene)-3-(N-benzyl)-indenylacetamide

5-Fluoro-2-methyl-3-(N-benzyl)-indenylacetamide from Example 1, part F is allowed to react with 1-acetyl-3-indolecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-acetyl-3-indolyl).

EXAMPLE 15

(Z)-5-Fluoro-2-methyl-(4-pyridinylidene-3-(N-2-fluorobenzyl)-indenylacetamide (A) 5-Fluoro-2-methyl-3-(N-2-fluorobenzyl)-indenylacetamide This compound is obtained from 5-fluoro-2-methylindenyl-3-acetyl chloride (Example 1E) using the procedure of Example 1, Part F and replacing benzylamine with 2-fluorobenzylamine.

(B) (Z)-5-Fluoro-2-methyl-(4-pyridinylidene)-3-(N-2-fluorobenzyl)-indenylacetamide 5-Fluoro-2-methyl-3-(N-2-fluorobenzyl)-indenylacetamide is allowed to react with 4-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridinyl).

EXAMPLE 16

(Z)-5-Fluoro-2-methyl-(3-pyridinylidene)-3-(N-2-fluorobenzyl)-indenylacetamide

5-Fluoro-2-methyl-3-(N-2-fluorobenzyl)-indenylacetamide from Example 15, part A is allowed to react with 3-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyridinyl).

EXAMPLE 17

(Z)-5-Fluoro-2-methyl-(2-pyridinylidene)-3-(N-2-fluorobenzyl)-indenylacetamide

5-Fluoro-2-methyl-3-(N-2-fluorobenzyl)-indenylacetamide from Example 15, part A is allowed to react with 2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=2-pyridinyl).

EXAMPLE 18

(Z)-5-Fluoro-2-methyl-(4-quinolinylidene)-3-(N-2-fluorobenzyl)-indenylacetamide

5-Fluoro-2-methyl-3-(N-2-fluorobenzyl)-indenylacetamide from Example 15, part A is allowed to react with 4-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-quinolinyl).

EXAMPLE 19

(Z)-5-Fluoro-2-methyl-(3-pyrazinylidene)-3-(N-2-fluorobenzyl)-indenylacetamide

5-Fluoro-2-methyl-3-(N-2-fluorobenzyl)-indenylacetamide from Example 15, part A is allowed to react with pyrazinealdehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrazinyl).

EXAMPLE 20

(Z)-5-Fluoro-2-methyl-(3-pyridazinylidene)-3-(N-2-fluorobenzyl)-indenylacetamide 5-Fluoro-2-methyl-3-(N-2-fluorobenzyl)-indenylacetamide from Example 15, part A is allowed to react with 3-pryidaziine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrazinyl).

EXAMPLE 21

(Z)-5-Fluoro-2-methyl-(3-pyrimidinylidene)-3-(N-2-fluorobenzyl)-indenylacetamide 5-Fluoro-2-methyl-3-(N-2-fluorobenzyl)-indenylacetamide from Example 15, part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$ H=H, $R_6$=H, $R_7$=F, n=1, m=1, Y=4-pyridazinyl).

EXAMPLE 22

(Z)-5-Fluoro-2-methyl-(4-pyridazinylidene)-3-(N-2-fluorobenzyl)-indenylacetamide 5-Fluoro-2-methyl-3-(N-2-fluorobenzyl)-indenylacetamide from Example 15, part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridazinyl).

EXAMPLE 23

(Z)-5-Fluoro-2-methyl-(4-pyridinylidene)-3-(N-(S-α-hydroxymethyl)benzyl)-indenylacetamide (A) 5-fluoro-2-methyl-3-(N-(S-α-hydroxylmethyl)benzyl)-indenylacetamide 5-Fluoro-2-methylindenyl-3-acetic acid (from Example 1D) (2.6 mmol) in DMA (2 ml) is allowed to react with n-(3-dimethylaminopropyl)-N'-ethylcarbodiimide hydrochloride (4 mmol) and S-2-amino-2-phenylethanol (3.5 mmol) at room temperature for two days. The reaction mixture is added dropwise to stirred ice water (50 ml). A white precipitate is filtered off, washed with water (5 ml), and dried in vacuo. Recrystallization from ethylacetate gives the desired compound.

(B) (Z)-5-Fluoro-2-methyl-(4-pyridinylidene)-3-(N-(S-α-hydroxvmethyl)benzyl)-indenylacetamide 5-Fluoro-2-methyl-3-(N-(S-α-hydroxylmethyl)benzyl)-indenylacetamide from part A is allowed to react with 4-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridinyl).

EXAMPLE 24

(Z)-5-Fluoro-2-methyl-(3-pyridinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with 3-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridinyl).

EXAMPLE 25

(Z)-5-Fluoro-2-methyl-(2-pyridinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with 2-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_{7=H,\ n=}$1, m=1, Y=3-pyridinyl).

EXAMPLE 26

(Z)-5-Fluoro-2-methyl-(4-quinolinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with 4-quinolinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-quinolinyl).

EXAMPLE 27

(Z)-5-Fluoro-2-methyl-(pyrazidinylidene)-3-(N-(S-α-hydroxymethyl)benzevl)-indenylacetamide 5-Fluoro-2-methyl-3-(N-(S-α-hydroxylmethyl)benzyl)-indenylacetamide from Example 23 part A is allowed to react with pryazidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=pyrazidinyl).

EXAMPLE 28

(Z)-5-Fluoro-2-methyl-(3-pyridazinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with pryidazine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, Y=3-pyridazinyl).

EXAMPLE 29

(Z)-5-Fluoro-2-methyl-(4-pyrimidinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyrimidinyl).

EXAMPLE 30

(Z)-5-Fluoro-2-methyl-(4-pyridazinylidene)-3-(N-(S-α-hydroxymethyl)benzyl)-indenylacetamide 5-Fluoro-2-methyl-3-(N-(S-α-hydroxylmethyl)benzyl)-indenylacetamide from Example 23 part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridazinyl).

EXAMPLE 31 rac-(Z)-5-Fluoro-2-methyl-(4-pyridinylidene)-3-(N-benzyl)Indenyl-α-iydroxyacetamide (A) 5-Fluoro-2-methyl-3-(N-benzyl-N-hydroxy)-indenylacetamide To a mixture of N-benzylhydroxylamine hydrochloride (12 mmol) and $Et_3N$ (22 mmol) in $CH_2Cl_2$ (100 ml) at 0° C. is added a cold solution of 5-fluoro-2-methylindenyl-3-acetyl chloride (Example 1, Step E) (10 mmol) in $CH_2Cl_2$ (75 ml) over a period of 45–60 minutes. The mixture is warmed to room temperature and is stirred for 1 hour. The mixture is diluted with water (100 ml), and the organic layer is washed with HCl (2×25 ml) and brine (2×100 ml), dried ($MgSO_4$) and evaporated. The crude product is purified with flash chromatography to give the title compound.

(B) 5-Fluoro-2-methyl-3-(N-benzyl-N-mesyloxy)-indenylacetamide

To a solution of 5-fluoro-2-methyl-3-(N-benzyl-N-hydroxy)-indenylacetamide (5 mmol) in $CH_2Cl_2$ (25 ml) at 0° C. is added triethylamine (5 mmol). The mixture is stirred for 10 minutes, and methanesulfonyl chloride (5.5 mmol) is added dropwise. The solution is stirred at 0° C. for 2 hours, allowed to warm to room temperature, and stirred for another 2 hours. The organic layer is washed with water (2×20 ml), in HCl (15 ml), and brine (20 ml) and dried over $MgSO_4$. After rotary evaporation, the product is purified with flash chromatography to give the title compound.

(C) rac-5-Fluoro-2-methyl-3-(N-benzyl)-α-hydroxvindenylacetamide

To a solution of 5-fluoro-2-methyl-3-(N-benzyl-N-mesyloxy)-indenylacetamide (2 mmol) in $CH_3CN/H_2O$ (12 ml. each) is added triethylamine (2.1 mmol) in $CH_3CN$ (24 ml) over a period of 6 hours. The mixture is stirred overnight. The solvent is removed, and the residue diluted with ethyl acetate (60 ml), washed with water (4×20 ml), in HCl (15 ml), and brine (20 ml) and dried over $MgSO_4$. After rotary evaporation, the product is purified by recrystallization to give the title compound.

(D) rac-(Z)-5-Fluoro-2-methyl-(4-pyridinylidene)-3-(N-benzyl)-indenyl-α-hydroxyacetamide is obtained from rac-5-fluoro-2-methyl-3-(N-benzyl)-α-hydroxyindenylacetamide using the procedure of Example 1, Part G ($R_1$=F, $R_2$=$CH_3$, $R_3$=OH, $R_4$=H, $R_5$=H, $R_6$=H, $R_7$=H, n=1, m=1, Y=4-pyridinyl).

EXAMPLE 32

2-[(Z)-5-Fluoro-2-methyl-(4-pridinylidene)-3-(N-bcnzyl)-indenyl]-oxyacetamide

For Pfitzner-moffatt oxidation, a solution of rac-(Z)-5-fluoro-2-methyl-(4-pyridinylidene)-3-(N-benzyl)-indenyl-α-hydroxyacetamide (1 mmol) in DMSO (5 ml) is treated with dicyclohexylcarbodiimide (3 mmol). The mixture is stirred overnight, and the solvent is evaporated. The crude product is purified by flash chromatography to give the title compound ($R_1$=F, $R_2$=$CH_3$, $R_3$ and R4 together form C=O, $R_5$=H, $R_6$=H, $R_7$=H, n=1, m=1, and Y=4-pyridinyl).

EXAMPLE 33 rac-(Z)-5-Fluoro-2-methyl-(4-pyridinylidene)-3-(N-benzyl)-indenyl-α-(2-propylamino)-acetamide (A) 5-Fluoro-2-methyl-3-(N-2-propyl-N-hydroxy)-indenylacetamide is obtained from 5-fluoro-2-methylindenyl-3-acetyl chloride (Example 1, Step E) using the procedure of Example 31, Part A and replacing N-benzylhydroxylamine hydrochloride with N-2-propyl hydroxylamine hydrochloride.

(B) 5-Fluoro-2-methyl-3-(N-2-propyl-N-mesyloxy)-indenylacetamide is obtained according to the procedure of Example 31, Part B.

(C) rac-5-Fluoro-2-methyl-3-(N-benzyl)-α-(2-propylamino)-acetamide. To 5-fluoro-2-methyl-3-(N-2-propyl-N-mesyloxy)-indenylacetamide (2 mmol) in $CH_2Cl_2$ (25 ml) at 0° C. is added benzylamine (4.4 mmol) in $CH_2Cl_2$ (15 ml) over a period of 30 minutes. The resulting solution is stirred at 0° C. for 1 hour, and at room temperature overnight. The solvent is removed, and the residue is treated with 1 N NaOH, and is extracted with $CH_2Cl_2$ (100 ml). The extract is washed with water (2×10 ml), and is dried over $MgSO_4$. After rotary evaporation, the product is purified by flash chromatography.

(D) rac-(Z)-5-Fluoro-2-methyl-(4-pyridinylidene)-3-(N-benzyl)-indenyl-α-(2-propylamino)-acetamide is obtained from rac-5-fluoro-2-methyl-3-(N-benzyl)-α-(2-propylamino)-acetamide using the procedure of Example 1, Part G ($R_1$=F, $R_2$=$CH_3$, $R_3$= isopropylamino, $R_4$=H, $R_5$=H, $R_6$=H, $R_7$=H, n=1, m=1, Y=4-pyridinyl).

EXAMPLE 34

(Z)-6-methoxy-2-methyl-(4-pyridinylidene)-3-(N-benzyl)-indenylacetamide (A) Ethyl-2-Hydroxy-2-(p-methoxyphenyl)-1-methylpropionate In a 500 ml. 3-necked flask is placed 36.2 g. (0.55 mole) of zinc dust, a 250 ml. addition funnel is charged with a solution of 80 ml. anhydrous benzene, 20 ml. of anhydrous ether, 80 g. (0.58 mole) of p-anisaldehyde and 98 g. (0.55 mole) of ethyl-2-bromoproplonate. About 10 ml. of the solution is added to the zinc dust with vigorous stirring, and the mixture is warmed gently until an exothermic reaction commences. The remainder is added dropwise at such a rate that the reaction mixture continues to reflux smoothly (ca. 30–35 min.). After addition is completed the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid and washed twice with 50 ml. portions of water. The combined aqueous acidic layers are extracted with 2×50 ml. ether. The combined etheral and benzene extracts are dried over sodium sulfate. Evaporation of solvent and fractionation of the residue through a 6" Vigreux column affords 89 g. (60%) of the product, ethyl-2-hydroxy-2-(p-methoxyphenyl)-1-methylpropionate, B. P. 165–160° (1.5 mm.).

(B) 6-Methoxy-2-methylindanone

By the method described in Vander Zanden, Rec. Trav. Chim., 68, 413 (1949), the compound from part A is converted to 6-methoxy-2-methylindanone.

Alternatively, the same compound can be obtained by adding α-methyl-β-(p-methoxylphenyl)propionic acid (15 g.) to 170 g. of polyphosphoric acid at 50° and heating the mixture at 83–90° for two hours. The syrup is poured into iced water. The mixture is stirred for one-half hour, and is extracted with ether (3×). The etheral solution is washed with water (2×) and 5% $NaHCO_3$ (5×) until all acidic material has been removed, and is dried over sodium sulfate. Evaporation of the solution gives 9.1 g. of the indanone as a pale yellow oil.

(C) (Z)-6-Methoxy-2-methyl-(4-pyridinylidene)-3-(N-benzyl)-indenylacetamide

In accordance with the procedures described in Example 1, parts D-G, this compound is obtained substituting 6-methoxy-2-methylindanone for 6-fluoro-2-methylindanone in part D of Example 1.

EXAMPLE 35

(Z)-S-Methoxy-2-methyl-(4-pyridinylidene)-3-(N-benzyl)-indenylacetamide (A) Ethyl 5-methoxy-2-methyl-3-indenvl Acetate A solution of 13.4 g of 6-methoxy-2-methylindanone and 21 g. of ethyl bromoacetate in 45 ml. benzene is added over a period of five minutes to 21 g. of zinc amalgam (prepared according to Org. Syn. Coll. Vol. 3) in 110 ml. benzene and 40 ml. dry ether. A few crystals of iodine are added to start the reaction, and the reaction mixture is maintained at reflux temperature (ca. 65°) with external heating. At three-hour intervals, two batches of 10 g. zinc amalgam and 10 g. bromoester are added and the mixture is then refluxed for 8 hours. After addition of 30 ml. of ethanol and 150 ml. of acetic acid, the mixture is poured into 700 ml. of 50% aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temperature)(1–2 mm.) gives crude ethyl-(1-hydroxy-2-methyl-6-methoxy-indenyl) acetate (ca. 18 g.).

A mixture of the above crude hydroxyester, 20 g. of p-toluenesulfonic acid monohydrate and 20 g. of anhydrous calcium chloride in 250 ml. toluene is refluxed overnight. The solution is filtered, and the solid residue is washed with toluene. The combined toluene solution is washed with water, sodium bicarbonate, water and then dried over sodium sulfate. After evaporation, the crude ethyl 5-methoxy-2-methyl-3-indenyl acetate is chromatographed on acid-washed alumina, and the product is eluted with petroleum ether-ether (v./v. 50–100%) as a yellow oil (11.8 g., 70%).

(B) (Z)-5-Methoxy-2-methyl-(4-pyridinylidene)-3-(N-benzyl)-indenylacetamide

In accordance with the procedures described in Example 1, parts E-G, this compound is obtained substituting ethyl-5-methoxy-2-methyl-3-indenyl acetate for 5-fluoro-2-methindenyl-3-acetic acid in Example 1, part E.

EXAMPLE 36

(Z)-α-5-Methoxy-2-methyl-(4-pyritinylidene)-3-(N-benzyl)-indenylpropionamide (A) α-(5-methoxy-2-methyl-3-indenyl)proipionic Acid The procedure of Example 35, part (A) is followed using ethyl α-bromopropionate in equivalent quantities in place of ethyl bromoacetate used therein. There is obtained ethyl α-(1-hydroxy-6-methoxy-2-methyl-1-indanyl)propionate, which is dehydrated to ethyl α-(5-methoxy-2-methyl-3-indenyl)propionate in the same manner.

The above ester is saponified to give α-(5-methoxy-2-methyl-3-indenyl)propionic acid.

(B) (Z)-α-5-Methoxy-2-methyl-(4-pyridinyl)-3-(N-benzyl)-(α-methyl)indenylpropionamide In accordance with the procedures described in Example 1, parts E-G, this compound is obtained substituting (α-5-methoxy-2-methyl-3-indenyl)propionic acid for 5-fluoro-2-methylindenyl-3-acetic acid in Example 1, part E.

EXAMPLE 37

(Z) α-Fluoro-5-methoxy-2-methyl-(4-pyridinylidene)-3-(N-benzyl)indenylacetamide (A) Methyl-5-methoxy-2-methyl-3-indenyl-α-fluoro Acetate A mixture of potassium fluoride (0.1 mole) and methyl-5-methoxy-2-methyl-3-indenyl-α-tosyloxy acetate (0.05 mole) in 200 ml. dimethylformnamide is heated under nitrogen at the reflux temperature for 2–4 hours. The reaction mixture is cooled, poured into iced water and then extracted with ether. The ethereal solution is washed with water, sodium bicarbonate and dried over sodium sulfate. Evaporation of the solvent and chromatography of the residue on an acid-washed alumina column (300 g.) using ether-petroleum ether (v./v. 20–50%) as eluent give the product, methyl-5-methoxy-2-methyl-3-indenyl-(α-fluoroacetate.

(B) (Z) α-Fluoro-5-methoxy-2-methyl-(4-pyridinylidene)-3-(N-benzyl)indenylacetamide In accordance with the procedures described in Example 1, parts E-G, this compound is obtained substituting methyl-5-methoxy-2-methyl-3-indenyl-α-fluoroacetate for 5-fluoro-2-methylindenyl-3-acetic acid in Example 1, part E.

For the introduction of the =CH—Y part in Scheme III, any of the appropriate heterocyclic aldehydes mav be used either directly in the base-catalyzed condensation or in a Wittig reaction in an alternative route. The aldehydes that may be used are listed in Table 1 below:

TABLE 1 pyrrol-2-aldehyde*
pyrimidine-2-aldehyde
6-methylpyridine-2-aldehyde*
1-methylbenzimidazole-2-aldehyde
isoquinoline-4-aldehyde
4-pyridinecarboxaldehyde*
3-pyridinecarboxaldehyde*
2-pyridinecarboxaldehyde*
4,6-dimethyl-2-pyridinecarboxaldehyde*
4-methyl-pyridinecarboxaldehyde*
4-quinolinecarboxaldehyde*
3-quinolinecarboxaldehyde*
2-quinolinecarboxaldehyde*
2-chloro-3-quinolinecarboxaldehyde*
pyrazinealdehyde
(Prepared as described by Rutner et al., JOC 1963, 28, 1898–99)
pyridazine-3-aldehyde
(Prepared as described by Heinisch et al., Monatshefte Fuer Chemie 108, 213–224, 1977)
pyrimidine-4-aldehyde
(Prepared as described by Bredereck et al., Chem. Ber. 1964, 97, 3407–17)
2-methyl-pyrimidine-4-aldehyde
(Prepared as described by Bredereck et al., Chem. Ber. 1964, 97, 3407–17)
pyridazine-4-aldehyde
(Prepared as described by Heinisch et al., Monatshefte Fuer Chemie 104, 1372–1382 (1973))

TABLE 1-continued 1-methylindole-3-carboxaldehyde*
1-acetyl-3-indolecarboxaldehyde*

*Available from Aldrich

The aldehydes above can be used in the reaction schemes above in combination with various appropriate amines to produce compounds with the scope of this invention. Examples of appropriate amines are those listed in Table 2 below:

TABLE 2 benzylamine
2,4-dimethoxybenzylamine
2-methoxybenzylamine
2-fluorobenzylamine
4-dimethylaminobenzylamine
4-sulfonaminobenzylamine
1-phenylethylamine (R-enantiomer)
2-amino-2-phenylethanol (S-enantiomer)
2-phenylglycinonitrile (S-enantiomer)

EXAMPLE 38

(Z)-5-Fluoro-2-methyl-(4-pyridylidene)-3-(N-benzyl)indenylacetamide Hydrochloride (Z)-5-Fluoro-2-methyl-(4-pyridylidene)-3-(N-benzyl) indenylacetamide (1396 g; MW 384.45; 3.63 mol) from Example 1 is dissolved at 45° C. in ethanol (28 L). Aqueous HCl (12 M; 363 mL) is added stepwise. The reaction mixture is heated under reflux for 1 hour, is allowed to cool to room temperature, then stored at −10° C. for 3 hours. The resulting solid is filtered off, is washed with ether (2×1.5 L) and is air-dried overnight. Drying under vacuum at 70° C. for 3 days gives (Z)-5-fluoro-2-methyl-(4-pyridylidene)-3-(N-benzyl)indenylacetamide hydrochloride with a melting point of 207–209° C. ($R_1$=F, $R_2$=$CH_3$, $R_3$=H, $R_4$=H, $R_5$=H, $R_6$=H, $R_7$=H, n=1, m=1, Y=4-pyridinyl·hydrochloride).

Yield: 1481 g (97%; 3.51 mol); MW: 420.91 g/mol. $^1$H-NMR (DMSO-$d_6$): 2.18 (s,3,=C—$CH_3$); 3.54 (s,2, =$CH_2$CO); 4.28 (d,2,$NCH_2$);6.71 (m,1,ar.); 7.17 (m,8,ar.); 8.11 (d,2,ar., AB system); 8.85 (m,1,NH); 8.95 (d,2,ar.,AB system); IR (KBr): 3432 NH; 1635 C=O; 1598 C=C.

EXAMPLE 39

(Z)-5-Fluoro-2-methyl-(4-pyridylidene)-3-(N-benzyl)-indenylacetamide p-methylbenzenesulfonate (Z)-5-fluoro-2-methyl-(4-pyridylene)-3-(N-benzyl) indenylacetamide (MW=384.46 g/mol; 5.21 mmol; 2 g) from Example 1 is dissolved in ethanol (50 ml). Solid p-toluenesulfonic acid monohydrate (MW=190.22 g/mol; 5.21 mmol; 991 mg) is added to the stirred solution. The reaction mixture is stirred for 12 hours at room temperature. The ethanol is evaporated in aspirator vacuum. The residue is dried in high vacuum to yield (Z)-5-fluoro-2-methyl-(4-pyridylidene)-3-(N-benzyl)-indenylacetamide p-methylbenzenesulfonate as an orange-red powder.

As to identifying structurally additional PDE10 inhibiting compounds besides those of Formula I that can be effective therapeutically for the purposesof this invention, one skilled in the art has a number of useful model compounds disclosed herein (as well as their analogs) that can be used as the bases for computer modeling of additional compounds having the same conformations but different chemically. For example, software such as that sold by Molecular Simulations Inc. release of WebLab® ViewerPro™ includes molecular visualization and chemical communication capabilities. Such software includes functionality, including 3D visualization of known active compounds to validate sketched or imported chemical structures for accuracy. In addition, the software allows structures to be superimposed based on user-defined features, and the user can measure distances, angles, or dihedrals.

In this situation, since the structures of active compounds are disclosed above, one can apply cluster analysis and 2D and 3D similarity search techniques with such software to identify potential new additional compounds that can then be screened and selected according to the selection criteria of this invention. These software methods rely upon the principle that compounds, which look alike or have similar properties, are more likely to have similar activity, which can be confirmed using the PDE selection criterion of this invention.

Likewise, when such additional compounds are computer-modeled, many such compounds and variants thereof can be synthesized using known combinatorial chemistry techniques that are commonly used by those of ordinary skill in the pharmaceutical industry. Examples of a few for-hire combinatorial chemistry services include those offered by New Chemical Entities, Inc. of Bothell Wash., Protogene Laboratories, inc., of Palo Alto, Calif., Axys, Inc. of South San Francisco, Calif., Nanosyn, Inc. of Tucson, Ariz., Trega, Inc. of San Diego, Calif., and RBI, Inc. of Natick, Mass. There are a number of other for-hire companies. A number of large pharmaceutical companies have similar, if not superior, in-house capabilities. In short, one skilled in the art can readily produce many compounds for screening from which to select promising compounds for treatment of neoplasia having the attributes of compounds disclosed herein.

Thus, with the chemical structures of desirable compounds presented herein and the cGMP binding site information, one skilled in the art can model, identify and select (using the selection criteria of this invention) other chemical compounds for use as therapeutics.

BIOLOGICAL EFFECTS (A) Cyclooxygenase (COX) Inhibition

COX catalyzes the formation of prostaglandins and thromboxane by the oxidative metabolism of arachidonic acid. The compound of Example 1 of this invention, as well as a positive control, (sulindac sulfide) were evaluated to determine whether they inhibited purified cyclooxygenase Type I (see Table 1 below).

The compounds useful in the practice of this invention were evaluated for inhibitory effects on purified COX. The COX was purified from ram seminal vesicles, as described by Boopathy, R. and Balasubramanian, J., 239:371–377, 1988. COX activity was assayed as described by Evans, A. T., et al., "Actions of Cannabis Constituents on Enzymes Of Arachidonate Metabolism Anti-inflammatory Potential," Biochem. Pharmacol., 36:2035–2037, 1987. Briefly, purified COX was incubated with arachidonic acid (100 µM) for 2.0 min at 37° C. in the presence or absence of test compounds. The assay was terminated by the addition of TCA, and COX activity was determined by absorbance at 530 nm.

TABLE 1

| EXAMPLE | COX I<br>% Inhibition(100 µM) |
|---|---|
| Sulindac sulfide | 86 |
| 1 | <25 |

The advantage of very low COX inhibition is that compounds of this invention can be administered to patients without the side effects normally associated with COX inhibition.

(B) cGMP PDE Inhibition

Compounds of this invention are also PDE2 and PDE5 inhibitors as taught in part U.S. patent application Ser. No. 09/046,739 filed Mar. 24, 1998, now abandoned. Compounds can be tested for inhibitory effect on phosphodiesterase activity using either the enzyme isolated from any tumor cell line such as HT-29 or SW-480. Phosphodiesterase activity can be determined using methods known in the art, such as a method using radioactive $^3$H cyclic GMP (cGMP) (cyclic 3',5'-guanosine monophosphate) as the substrate for PDE5 enzyme. (Thompson, W. J., Teraski, W. L., Epstein, P. M., Strada, S. J., Advances in Cyclic Nucleotide Research, 10:69–92, 1979, which is incorporated herein by reference). In brief, asolution of defined substrate $^3$H-cGMP specific activity (0.2 µM; 100,000 cpm; containing 40 mM Tris-HCl (pH 8.0), 5 mM $MgCl_2$ and 1 mg/ml BSA) is mixed with the drug to be tested in a total volume of 400µl. The mixture is incubated at 30° C. for 10 minutes with partially purified cGMP-specific PDE isolated from HT-29 cells. Reactions are terminated, for example, by boiling the reaction mixture for 75 seconds. After cooling on ice, 100 µl of 0.5 mg/ml snake venom (O. Hannah venom available from Sigma) is added and incubated for 10 min at 30° C. This reaction is then terminated by the addition of an alcohol, e.g. 1 ml of 100% methanol. Assay samples are applied to a anion chromatography column (1 ml Dowex, from Aldrich) and washed with 1 ml of 100% methanol. The amount of radioactivity in the breakthrough and the wash from the columns in then measured with a scintillation counter. The degree of PDE5 inhibition is determined by calculating the amount of radioactivity in drug-treated reactions and comparing against a control sample (a reaction mixture lacking the tested compound).

Using such protocols, the compound of Example 1 had an $IC_{50}$ value for PDE5 inhibition of 0.68 µM. Using similar protocols, the compound of Example 38 ("Compound 38") had an $IC_{50}$ value for PDE2 of 14 µM, an $IC_{50}$ value for PDE5 of 4 µM, an $IC_{50}$ value for PDEI of 3 µM, and an $IC_{50}$ value for PDE4 of 6 µM.

(C) Safety Assessment in Mammals

As one skilled in the art will recognize from the data presented below, Compound 38 can safely be given to animals at doses far beyond the tolerable (and in many cases toxic) doses of conventional renal cell carcinoma therapies. For example, in an acute toxicity study in rats, single oral doses of Compound 38 administered (in a 0.5% carboxymethylcellulose vehicle) at doses up to and including 2000 mg/kg resulted in no observable signs of toxicity. At 2000 mg/kg, body weight gains were slightly reduced. A single dose of 1000 mg/kg administered intraperitoneally resulted in reduced body weight gain, with mesenteric adhesions seen in some animals from this group at necropsy.

In dogs, the administration of Compound 38 in capsules at 1000 mg/kg resulted in no signs of toxicity to the single group of two male and two female dogs. Due to the nature of Compound 38 capsules, this dose necessitated the use of at least 13 capsules to each animal, which was judged to be the maximum number without subjecting the animals to stress. Therefore, these dogs were subsequently administered seven consecutive doses of 1000 mg/kg/day. At no time in either dosing phase were any obvious signs of drug-related effects observed.

Thus, on a single-dose basis, Compound 38 is not acutely toxic. Based on the findings of these studies, the oral $LD_{50}$ of Compound 38 was considered to be greater than 1000 mg/kg in dogs and 2000 mg/kg in rats, and the intraperitoneal $LD_{50}$ was considered to be greater than 1000 mg/kg in rats.

A seven-day dose-range finding study in rats, where Compound 38 was evaluated by administering it at doses of 0, 50, 500 or 2000 mg/kg/day resulting in no observable signs of toxicity at 50 mg/kg/day. At 500 mg/kg/day, treatment-related effects were limited to an increase in absolute and relative liver weights in female rats. At 2000 mg/kg/day, effects included labored breathing and/or abnormal respiratory sounds, decreased weights gains and food consumption in male rats, and increased liver weights in female rats. No hematological or blood chemistry changes nor any microscopic pathology changes, were seen at any dose level.

A 28-day study in rats was also carried out at 0, 50, 500 and 2000 mg/kg/day. There were no abnormal clinical observations attributed to Compound 38, and body weight changes, ophthalmoscopic examinations, hematological and blood chemistry values and urinalysis examinations were unremarkable. No macroscopic tissue changes were seen at necropsy. Organ weight data revealed statistically significant increase in liver weights at 2000 mg/kg/day, and statistically significant increases in thyroid weights for the 2000 mg/kg/day group. The slight liver and thyroid increases at the lower doses were not statistically significant. Histopathological evaluation of tissues indicated the presence of traces of follicular cell hypertrophy, increased numbers of mitotic figures (suggestive of possible cell proliferation) in the thyroid gland and mild centrilobular hypertrophy in the liver. These changes were generally limited to a small number of animals at the 2000 mg/kg/day dose, although one female at 500 mg/kg/day had increased mitotic figures in the thyroid gland. The findings in the liver may be indicative of a very mild stimulation of liver microsomal enzymes, resulting in increased metabolism of thyroid hormones, which in turn resulted in thyroid stimulation.

A long-term safety assessment study was conducted in rats to investigate Compound 38 at 50, 200 and 500 mg/kg/day following repeated oral dosing for 91 consecutive days. Orally administered Compound 38 did not produce any major toxicological effects in rats. The only finding was a dose-related trend to increased liver and thyroid/parathyroid weights noted in males and females at 200 and 500 mg/kg/day. Microscopically, slight hepatocellular hypertrophy at 200 and 500 mg/kg/day groups, follicular cell hypertrophy at 500 mg/kg/day and increase in accumulation of hyalin droplets in the kidneys at 200 and 500 mg/kg/day group. However, no changes in clinical biochemistry and hematology were evident. These changes were not associated with any gross clinical abnormality.

Dogs were also dosed orally with Compound 38 at 50, 150 and 300 mg/kg/day for 91 consecutive days. There were no toxicological effects in the dog following 91 days of dosing. Orange discoloration of the feces (same color as Compound 38) was seen in the 150 and 300 mg/kg/day groups. This finding suggested that most of Compound 38 was being eliminated via the feces. Slightly lowered body weights were noted in the highest dose group. This dose was also associated with increased liver weights. However, there were no microscopic alterations to support the increase in liver weight. Therefore, we concluded that Compound 38 is well tolerated in the dog.

Also as to safety, in a single, escalating dose normal human volunteer clinical trial, patients, in which the drug was taken orally, Compound 38 produced no significant side effects at any dose (i.e., 50 mg–700 TDD). In addition, in a phase I trial, 21 patients with a range of solid tumors and good performance status received Compound 38 orally twice daily for 28 consecutive days. Cycles were repeated without a treatment-free interval. Doses ranged from 100 to 800 mg/day. Therapy was well tolerated overall and a maximum tolerated dose was not reached. Compound 38 is minimally toxic up to 800 mg TDD when administered orally on a twice-daily schedule.

One skilled in the art should recognize that in most of these animal and human studies any of the side effects observed occurred at very high doses, in excess of recommended human doses and are extremely minimal compared to what one would expect with many other drugs.

Screening Methodologies

To identify new compounds that inhibit PDE10 in the manner of this invention, one can retrace what we have taught in this application. Namely, a compound according to this invention can be found by evaluating its ability to inhibit PDE10 as taught above. Alternatively, the compound can be identified by its ability to inhibit cGMP PDEs non-selectively, (i.e., at least inhibit PDE10 and PDE2 and PDE5. It is also believed to be desirable to inhibit PDE1). As confirmation that a desired compound has been identified, one can then assess whether PDE10 is inhibited, and as further confirmation the compound causes cell death, preferably by apoptosis. These procedures are described above, and individually, but not in combination, known in the art.

To avoid a side effect that may or may not be desired, one can then assess whether the compound inhibits a cyclooxygenase enzyme. These methodologies are known as well. We suggest that an inhibitor so selected have an $IC_{50}$ for PDE10 of no more than about 25 $\mu$M. and has an $IC_{50}$ for each of the COX I and II enzymes greater than about 40 $\mu$M.

As one skilled in this art will appreciate, there are various ways to assess whether a compound inhibits, activates, modifies (e.g., phosphorylates) etc. a particular protein target. We do not mean to suggest that the specific tests we have described herein are the only such tests. Other methods of covalent modification, for example, would suffice.

It will be understood that various changes and modifications can be made in the details of procedure, formulation and use without departing from the spirit of the invention, especially as defined in the following claims.

We claim:

1. A method of treating renal cell carcinoma in a mammal with that disease comprising administering to the mammal a physiologically effective amount of an inhibitor of PDE10.

2. The method of claim 1 wherein said inhibitor does not substantially inhibit COX I or COX II.

3. The method of claim 1 wherein said mammal is also administered an inhibitor of PDE2.

4. The method of claim 1 wherein said mammal is also administered an inhibitor of PDE5.

5. The method of claim 3 wherein said mammal is also administered an inhibitor of PDE5.

6. The method of claim 5 wherein said inhibitor of PDE10, PDE2 and PDE5 comprise the same compound.

7. The method of claim 1 wherein said inhibitor is administered without an NSAID or exisulind.

8. The method of claim 1 wherein said inhibitor has an $IC_{50}$ for PDE10 of no more than about 25 $\mu$M. and has an $IC_{50}$ for each of the COX I and II enzymes greater than about 40 $\mu$M.

* * * * *